United States Patent
Xu et al.

(10) Patent No.: US 8,809,407 B2
(45) Date of Patent: *Aug. 19, 2014

(54) EXPANDABLE FUNCTIONAL TFE COPOLYMER FINE POWDER, EXPANDED PRODUCTS AND REACTED PRODUCTS THEREFROM

(71) Applicant: W. L. Gore & Associates, Inc., Newark, DE (US)

(72) Inventors: Ping Xu, Hockessin, DE (US); Jack J Hegenbarth, Wilmington, DE (US); Xin Kang Chen, Shanghai (CN); Rachel Radspinner, Flagstaff, AZ (US); Paul D Drumheller, Flagstaff, AZ (US); William B Johnson, Newark, DE (US); Wen K Liu, Newark, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,955

(22) Filed: Nov. 26, 2012

(65) Prior Publication Data

US 2013/0084460 A1 Apr. 4, 2013

Related U.S. Application Data

(63) Continuation of application No. 12/886,817, filed on Sep. 21, 2010, now Pat. No. 8,658,707, which is a continuation-in-part of application No. 12/410,050, filed on Mar. 24, 2009.

(51) Int. Cl.
| | |
|---|---|
| *C08J 9/16* | (2006.01) |
| *C08F 214/26* | (2006.01) |
| *C08F 228/02* | (2006.01) |
| *C08F 220/50* | (2006.01) |
| *C08F 220/28* | (2006.01) |
| *A61L 31/16* | (2006.01) |
| *C08L 27/18* | (2006.01) |
| *C08J 5/22* | (2006.01) |
| *C08F 14/26* | (2006.01) |
| *A61L 31/04* | (2006.01) |
| *C08J 9/28* | (2006.01) |
| *B29C 55/00* | (2006.01) |
| *B01J 39/18* | (2006.01) |
| *C08J 9/35* | (2006.01) |
| *B29K 105/04* | (2006.01) |
| *B29K 27/18* | (2006.01) |

(52) U.S. Cl.
CPC .......... *A61L 31/041* (2013.01); *B29K 2105/04* (2013.01); *B29K 2995/0092* (2013.01); *C08F 220/28* (2013.01); *C08F 214/26* (2013.01); *A61L 31/16* (2013.01); *C08L 27/18* (2013.01); *C08J 5/2237* (2013.01); *B29K 2027/18* (2013.01); *C08L 2205/02* (2013.01); *C08F 214/262* (2013.01); *C08F 220/50* (2013.01); *C08F 214/265* (2013.01); *C08F 14/26* (2013.01); *C08J 2201/0502* (2013.01); *A61L 31/048* (2013.01); *C08J 9/28* (2013.01); *C08J 2327/18* (2013.01); *B29C 55/005* (2013.01); *B01J 39/18* (2013.01); *C08J 9/35* (2013.01); *C08F 228/02* (2013.01)

USPC ............. 521/50.5; 521/56; 521/134; 521/145

(58) Field of Classification Search
USPC .............. 521/50.5, 56, 134, 145, 27; 428/422
See application file for complete search history.

(56) References Cited

U.S. PATENT DOCUMENTS

| | | |
|---|---|---|
| 3,692,569 A | 9/1972 | Grot |
| 3,953,566 A | 4/1976 | Gore |
| 3,962,153 A | 6/1976 | Gore |
| 4,016,345 A | 4/1977 | Holmes |
| 4,036,802 A * | 7/1977 | Poirier .......................... 523/323 |
| 4,187,390 A | 2/1980 | Gore |
| 4,326,046 A | 4/1982 | Miyaka et al. |
| 4,792,594 A | 12/1988 | Gangal et al. |
| 4,902,423 A | 2/1990 | Bacino |
| 4,985,296 A | 1/1991 | Mortimer |
| 5,190,822 A | 3/1993 | Nishikawa et al. |
| 5,476,589 A | 12/1995 | Bacino |
| 5,608,022 A | 3/1997 | Nakayama et al. |
| 5,708,044 A | 1/1998 | Branca |
| 5,814,405 A | 9/1998 | Branca et al. |
| 5,874,165 A | 2/1999 | Drumheller |
| 5,897,955 A | 4/1999 | Drumheller |

(Continued)

FOREIGN PATENT DOCUMENTS

| | | |
|---|---|---|
| EP | 41737 | 12/1981 |
| EP | 1085051 | 3/2001 |

(Continued)

OTHER PUBLICATIONS

American Chemical Society Symposium, 1982, Series 180.
Aumsuwan, Nattharika et al; Antibacterial Surfaceson Expanded Polytetrafluoroethylene; Penicillin Attachment; Biomacromolecules; 2007; 713-718.
Ebnesajjad, Sina; Fluoroplastics vol. 1: Non-Melt Processible Fluoroplastics The Definitive User's Guide and Databook; (2000) p. 19,Williams Andrew, Inc. Norwich, NY.
Ebnesajjad,Sina, Fluoroplastics—vol. 2, Melt Processible Fluoropolymers, 2003, Chapters 1, 2, 3, 5, 8, Williams Andrew Inc., Norwich NY, USA.

(Continued)

*Primary Examiner* — Annop Singh
*Assistant Examiner* — Anna Falkowitz
(74) *Attorney, Agent, or Firm* — Amy L. Miller

(57) ABSTRACT

A functional TFE copolymer fine powder is described, wherein the TFE copolymer is a polymer of TFE and at least one functional comonomer, and wherein the TFE copolymer has functional groups that are pendant to the polymer chain. The functional TFE copolymer fine powder resin is paste extrudable and expandable. Methods for making the functional TFE copolymer are also described. The expanded functional TFE copolymer material may be post-reacted after expansion.

23 Claims, 4 Drawing Sheets

(56) References Cited

U.S. PATENT DOCUMENTS

| | | |
|---|---|---|
| 5,914,182 A | 6/1999 | Drumheller |
| 5,916,585 A | 6/1999 | Cook et al. |
| 5,972,449 A | 10/1999 | Chung |
| 6,127,486 A | 10/2000 | Burger et al. |
| 6,143,675 A | 11/2000 | McCollam et al. |
| 6,177,533 B1 | 1/2001 | Woodward |
| 6,254,978 B1 | 7/2001 | Bahar et al. |
| 6,273,271 B1 | 8/2001 | Moya |
| 6,461,665 B1 | 10/2002 | Scholander et al. |
| 6,541,589 B1 | 4/2003 | Baillie |
| 7,019,083 B2 | 3/2006 | Grootaert et al. |
| 7,306,729 B2 | 12/2007 | Bacino et al. |
| 7,342,066 B2 | 3/2008 | Dadalas et al. |
| 7,531,611 B2 | 5/2009 | Sabol et al. |
| 2005/0187363 A1 | 8/2005 | Oharu et al. |
| 2005/0197458 A1 | 9/2005 | Kuboyama |
| 2005/0222319 A1 | 10/2005 | Baillie |
| 2006/0270780 A1 | 11/2006 | Xu et al. |
| 2007/0010642 A1 | 1/2007 | Sabol et al. |
| 2007/0072036 A1 | 3/2007 | Berta et al. |
| 2007/0154651 A1 | 7/2007 | Weiss et al. |
| 2008/0061472 A1 | 3/2008 | Kennedy et al. |
| 2008/0139689 A1 | 6/2008 | Huang et al. |
| 2009/0093602 A1 | 4/2009 | Ford |
| 2010/0130690 A1 | 5/2010 | Nanba et al. |
| 2010/0159143 A1 | 6/2010 | Moya et al. |

FOREIGN PATENT DOCUMENTS

| | | |
|---|---|---|
| EP | 1535935 | 6/2005 |
| EP | 1681308 | 7/2006 |
| EP | 1746130 | 1/2007 |
| EP | 1939222 | 7/2008 |
| EP | 1947144 * | 7/2008 |
| GB | 1523047 | 8/1978 |
| GB | 2014870 | 9/1979 |
| JP | 5692943 | 12/1980 |
| JP | 7118348 | 5/1995 |
| JP | 2007146173 | 6/1995 |
| JP | 11035766 | 7/1998 |
| JP | 11240918 | 2/1999 |
| JP | 2010037365 | 2/2010 |
| RU | 2271367 | 10/2000 |
| RU | 2315777 | 12/2002 |
| SU | 2103283 | 7/1991 |
| WO | 03/050150 | 6/2003 |
| WO | 2007/052664 | 5/2007 |
| WO | WO2007052664 | 10/2007 |
| WO | 2008/001894 | 1/2008 |
| WO | WO2009/045423 | 4/2009 |

OTHER PUBLICATIONS

Hermanson, GT, Bioconjugate Techniques, 2nd Ed, Academic Press (Amsterdam) 2008, Chapters 1-8, 13-15, 17-18, 22-27.

Inagaki, N. Ph.D., Plasma Surface Modification and Plasma Polymerization, 1996, 44.

Jin, Gu et al.; Surface Modifying of Microporous PTFE Capillary for Bilirubin Removing from Human Plasma and Its Blood Compatibility; Materials Science and Engineering C; 2008; 1480-1488.

Li, Da-Feng et al.; Prepration of a Hydrophobic Polythiophene Film to Improve Protein Adsorption and Proliferation of PC 12 Cells; J. Phys. Chem. B 2008, 112 (51), 16290-16299.

Moore, Albert L.; Fluoroelastomers Handbook The Definitive User's Guide and Databook; Williams Andrew, Inc. Norwich NY, (2006) p. 33.

Mosbach, K. (Ed), Methods in Enzymology, Immobilized Enzymes and Cells, 1987, Part B, vol. 125, Academic Press (Orlando).

Wong, S.S., Chemistry of Protein Conjugation and Cross-Linking, Chapters 2-6 and 12, 1993, CRC Press (Boca Raton).

Partial International Search Report, PCT/US2010/000810, 2 pages.

International Search Report, PCT/US2010/000810, Oct. 13, 2010, 12 pages.

International Search Report, PCT/US2011/043341, Sep. 19, 2011, 3 pages.

International Search Report, PCT/US2011/049058, Feb. 14, 2012, 3 pages.

"Definitions of Terms Relating to Crystalline Polymers (1988)," 15 pages, (May 18, 2001), www.lupac.org.

* cited by examiner

EXPANDABLE FUNCTIONAL TFE COPOLYMER FINE POWDER, EXPANDED PRODUCTS AND REACTED PRODUCTS THEREFROM

RELATED APPLICATION

The present application is a divisional application of U.S. patent application Ser. No. 12/886,817 filed Sep. 21, 2010 which is a continuation-in-part application of pending U.S. patent application Ser. No. 12/410,050 filed Mar. 24, 2009

FIELD OF THE INVENTION

Expandable TFE copolymer fine powder resins containing functional monomers, expanded functional products obtained from these copolymers, and processes for making them are described herein. Further described are post-expansion reactions of the expanded functional TFE copolymer materials, and products made therefrom.

BACKGROUND OF THE INVENTION

Polytetrafluoroethylene or PTFE is known to have a unique combination of properties including excellent chemical resistance, thermal stability at high temperature, low surface energy and excellent electrical (dielectric) properties. PTFE is also known to have two deficiencies which limit its use high cold flow or creep and poor resistance to ionizing radiation.

Stretching certain forms of PTFE to make microporous expanded PTFE (ePTFE) can improve strength, decrease cold flow or creep, and improve the dielectric properties without changing surface or chemical properties. The chemical resistance or inertness, as well as the low surface energy, of PTFE and ePTFE are beneficial properties for some applications. But for other applications, it would be beneficial to selectively modify these properties without degrading the polymer.

There has been significant research to modify the surface or chemical properties of PTFE and microporous ePTFE in order to improve adhesion and compatibility with other materials. For example, efforts have included attempts to decrease creep by radiation crosslinking, increase or decrease the surface free energy (e.g. increase or decrease hydrophilicity), and provide sites for chemical reactions to improve the utility of PTFE and/or ePTFE in specific applications by chemical and plasma treatments.

Recently, plasma treatment of microporous ePTFE in the presence of maleic anhydride is reported to have produced acid functionality on the surface of the microporous ePTFE. Though the exact mechanism of these surface reactions is not reported, it likely results from the formation of free radicals by bond scission. Where carbon-carbon bond strength is known to be about forty percent lower than carbon-fluorine bonds, a majority of the radicals would result from scission of the carbon-carbon bonds, or main polymer chain scission, thereby decreasing the molecular weight of the polymer, and restricting the anhydride or acid functionality to the ends of the degraded polymer chains. Plasma graft polymerization is restricted near the surface of the sample. (Plasma Surface Modification and Plasma Polymerization; N. Inagoki, Technomic Publishing, 1996, p. 44).

Techniques for dispersion polymerization of both tetrafluoroethylene (TFE) monomer and TFE copolymers have been described. There are references which define and distinguish TFE copolymers based on the concentration of the comonomer. TFE polymers containing less than 1 weight percent comonomer have been referred to as modified homopolymers, or modified PTFE, whereas TFE polymers containing more than 1 weight percent comonomer have been referred to as TFE copolymers. (Fluoroplastics—Vol 1: Non-Melt Processible Fluoroplastics; Williams Andrew, Inc., Norwich, N.Y., at p. 19 (2000).) However, for use herein, TFE polymers containing one or more comonomers at any concentration will be defined as TFE copolymers.

In some processes, dispersion polymerization of TFE produces a resin that has come to be known as "fine powder." (e.g., U.S. Pat. No. 4,016,345 (Holmes, 1977)). Generally, in such processes, sufficient dispersing agent is introduced into a water carrier such that, upon addition of TFE monomer in the presence of a suitable polymerization initiator and, upon agitation and under autogenous TFE pressure of 10-40 kg/cm$^2$, polymerization proceeds until the desired level of colloidally dispersed polymer particles is reached and the reaction is then stopped. The dispersed polymer particles may subsequently be coagulated by known techniques to obtain the fine powder form of the polymer. The fine powders are dried at temperatures from about 100 to 200° C.

Fine powder resins are known to be useful in paste extrusion processes and in stretching (expansion) processes in which the paste-extruded extrudate, after removal of extrusion aid lubricant, is stretched to produce porous, strong products of various cross-sectional shapes such as rods, filaments, sheets, tubes, etc. Such a stretching process is disclosed in commonly owned U.S. Pat. No. 3,953,566 ("'566" to Gore). The expansion process as it applies to fluorocarbon polymers is described in the aforesaid '566 patent. As used herein, articles that can be expanded by the process of the '566 patent are said to be "expanded" and the resins used in the expansion process to create such articles are said to be expandable TFE polymers or expandable TFE copolymers.

Dispersion processes to make TFE copolymers are taught in for example, in U.S. Pat. No. 4,792,594 (Gangal et al.), U.S. Pat. No. 6,541,589 (Baillie), U.S. Pat. App. 2007/0010642 (Sabol and Baillie) and U.S. patent application Ser. No. 11/906,877 (Ford; filed Oct. 4, 2007). Dispersion processes to make copolymers are also described. It is taught that fine powders made by these dispersions may be paste extruded and processed by the processes disclosed in U.S. Pat. No. 3,953,566 to make microporous expanded products. TFE fine powder polymer processed by paste extrusion or expansion has high crystallinity especially for the portion of polymer formed in the later stage of the polymerization. This material is sometimes described as the shell or the sheath of the dispersion particle.

TFE copolymers processable by melt extrusion and injection molding include TFE-HFP (hexafluoropropylene) copolymers known as FEP, TFE perfluoroalkyl vinyl ether copolymers known as PFA and MFA, and TFE ethylene copolymers known as E-TFE. These polymers are not fine powders and cannot be paste extruded or expanded into microporous products because of low crystallinity.

TFE copolymers made from fluorovinyl ether comonomers having sulfonyl fluoride groups, ester groups and cyano groups have been described having the formulae:

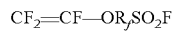   I.

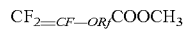   II.

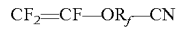   III.

where R$_f$ is fluoroalkyl or fluoroalkyl ether. (Fluoroplastics—Vol. 2: Melt Processible Fluoropolymers; Williams Andrew Inc,; Perfluorinated Ionomer Membranes, American Chemical Society Symposium, Series 180, 1982; U.S. Pat. No.

3,692,569 (Grot); Moore, Albert L. *Fluoroelastomers Handbook*, William Andrew Publishing, 2006).

Monomers of structures I and II are copolymerized with TFE to form polymers subsequently hydrolyzed to form the sulfonic acid and carboxylic acid. However, these polymers contain sufficient concentration of comonomer that there is little if any crystallinity in the polymers. Monomers of structure III have been polymerized with TFE and perfluoroalkylvinyl ethers to make perfluoro elastomers where monomer with structure III is the cross link site for the elastomers. The materials have little or no crystallinity and are therefore not expandable to create microporous materials.

U.S. Pat. App. 2006/0270780 (Xu et al.) teaches a PTFE modified with a cyanovinyl ether cross linking monomer in a microemulsion process. In this patent application, the modified PTFE is not a fine powder and cannot be paste extruded and expanded according to the '566 process.

U.S. Pat. No. 7,019,083 (Grootaert) teaches low molecular weight melt processable TFE perfluoropropylvinyl ether (PPVE) copolymer containing a cyanovinyl ether that is not formed as a fine powder and which would lack sufficient crystallinity to be paste extruded and be processed into microporous products. U.S. Pat. No. 4,326,046 (Miyake) teaches making modified PTFE by including 0.001 to 10 mol % of a comonomer component having an acid type functional (or precursor to an acid) group. The acid includes carboxylic, sulphonic or phosphoric acids. U.S. Pat. No. 4,326,046, teaches that the particle of the modified polytetrafluoroethylene comprises a core made of homopolymer of tetrafluoroethylene and the modifier component is included in the sheath layer. U.S. Pat. No. 4,326,046 does not teach paste extruding or expanding the modified polymer. Materials having the high modifier component polymerized in the later stages of polymerization would not have sufficient crystallinity to be processed into microporous products by the '566 process.

U.S. Pat. No. 7,342,066 to Dadalas et al. teaches use of a PTFE dispersion in a coating process. The PTFE contains up to 1 weight percent of an ionic comonomer (e.g., a monomer having acid groups such as an ionic group) where at least a portion and preferably all of the comonomer is added in the later stage of the polymerization. U.S. Pat. No. 7,342,066 does not teach forming a paste extrudable or expandable fine powder. Materials made with the high comonomer concentration at the later stages of polymerization would have low crystallinity and would not be paste extrudable or expanded by the processes of the '566 patent.

There is a need for TFE copolymer materials containing functional groups which impart specific chemical properties to a polymer, wherein the copolymer can be expanded to provide a microstructure characterized by nodes interconnected by fibrils. There is a further need for expanded TFE copolymer materials containing functional groups that can undergo subsequent controlled reactions to impart other specific properties to the expanded material while maintaining properties of the expanded TFE copolymer material.

SUMMARY OF THE INVENTION

This invention relates to functional TFE copolymers comprising TFE and at least one comonomer that comprises a functional group. The functional TFE copolymer has functional groups that are pendant to the polymer chain. The pendant functional groups emanate from a branch in the polymer chain. The functional TFE copolymer can be expanded (stretched under controlled conditions) to produce microporous expanded TFE copolymer material, having a microstructure characterized by nodes (1) interconnected by fibrils (2) (as exemplified in FIGS. 1 and 2).

A process for polymerization of these monomers to produce functional TFE copolymers is described, as well as dispersions of the functional TFE copolymer. Moreover, functional TFE copolymer fine powder is described that is paste extrudable and expandable into microporous functional TFE copolymers. The porous functional products produced by expansion of the polymers, and reactions of the porous functional TFE copolymeric materials are described.

DETAILED DESCRIPTION OF THE INVENTION

Figure 1:
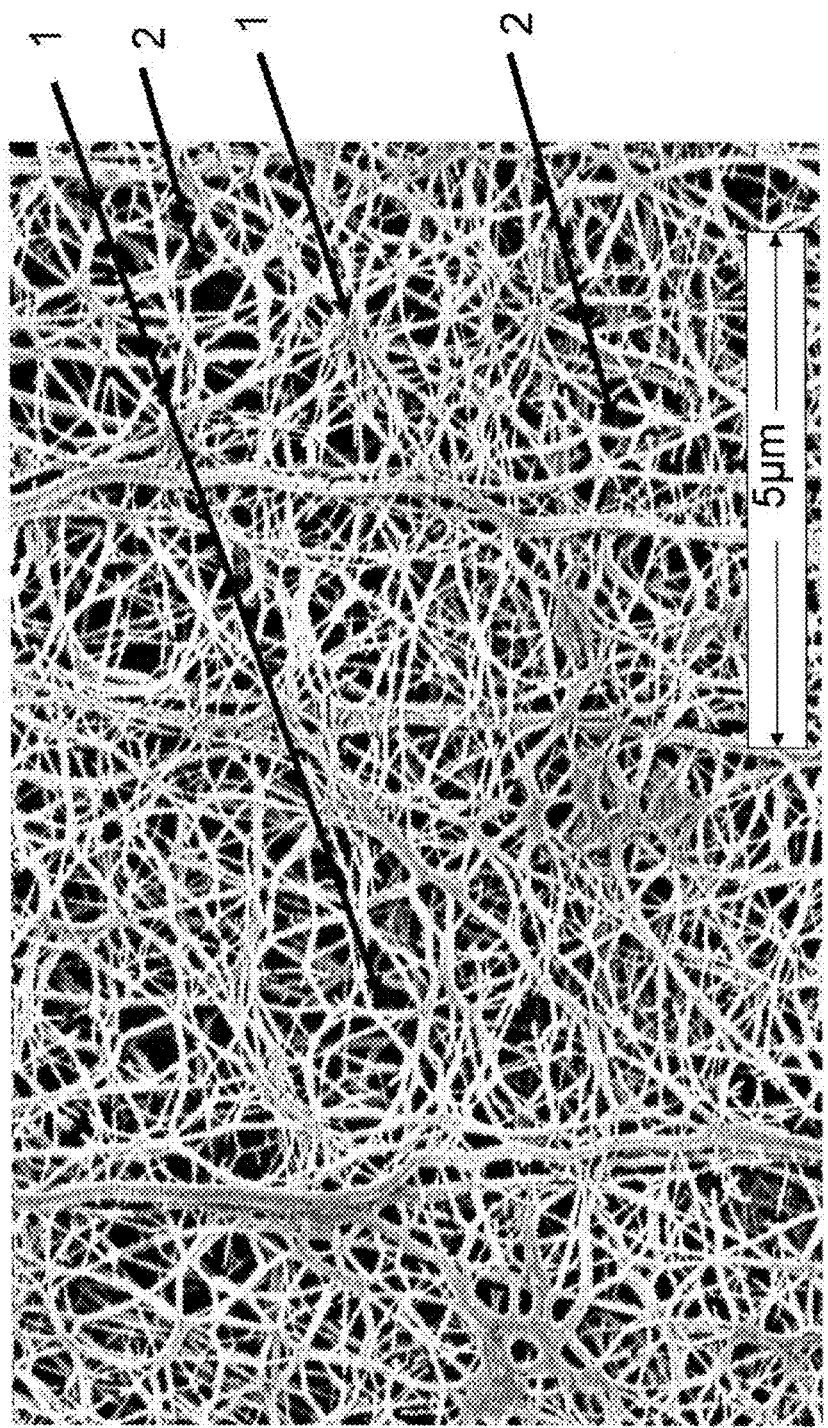
FIG. 1 SEM photomicrograph of an expanded sheet of functional TFE copolymer taken at 10,000× magnification.

Described herein are functional TFE copolymers made from an aqueous dispersion polymerization process, and processes for forming fine powders of the functional TFE copolymers that are paste-extrudable and expandable. The functional TFE copolymer comprises a polymer of TFE and at least one comonomer that contains a functional group. The TFE copolymers comprise functional groups that are pendant to the polymer chain. A process is provided for making the functional TFE copolymer fine powder from TFE and at least one comonomer containing a functional group. Further described is the microporous expanded TFE copolymer having functional groups obtained from the fine powders, and processes for reacting the microporous expanded TFE copolymer having functional groups.

The term TFE copolymer is defined as a TFE polymer comprising one or more comonomer at any concentration. As used herein the term functional TFE copolymer is defined as a TFE copolymer having functional groups that are pendant to the polymer chain wherein the functional TFE copolymer is formed by copolymerizing TFE with comonomers having a functional group. The functional TFE copolymers may be expanded into microporous materials. The expanded functional TFE copolymers made by the processes described herein have a microstructure characterized by nodes interconnected by fibrils and the copolymers have a functional group pendant to the polymer chain.

As used herein, the term functional comonomer is a monomer that copolymerizes with TFE in a dispersion polymerization and when incorporated into the polymer introduces side groups comprising functional groups that are pendant to the polymer chain. Functional comonomers which may be useful in this invention include fluorinated and perfluorinated monomers. Fluorinated monomers contain at least one fluorine atom. Perfluorinated monomers have at least one fluorine atom, and no carbon-hydrogen bonds and no carbon-halogen bonds other than carbon-fluorine bonds. Suitable functional monomers have the general formulae given in Table 1 where Z is defined as the functional group, examples of which are provided in Table 2.

TABLE 1

General structural formulae for comonomers

| | |
|---|---|
| $CX_2=CXZ$ | X: H, halogen, alkyl, fluoro alkyl |
| $CX_2=CX-R-Z$ | X: H, halogen, alkyl, fluoro alkyl |
| | R: alkyl, alkyl ether, fluoro alkyl ether, perfluoro alkyl ether |
| $CF_2=CF-O-R_f-Z$ | $R_f$: fluoro alkyl or fluoro alkyl ether |

Functional groups which may be incorporated into the copolymers as pendant groups, include but are not limited to the functional groups listed in Table 2. As used herein, the term functional group specifically excludes ether groups (C—O—C), and groups formed by carbon-halogen or carbon-hydrogen bonds. These bonds are described as —$CX_2$— or —$CX_3$ where X is either halogen or hydrogen. For purposes herein, while chemical moieties including ether groups, and chemical moieties formed from carbon-halogen bonds and carbon-hydrogen bonds, are not considered functional groups, they may be part of a functional comonomer comprising a functional group that is suitable for use herein.

TABLE 2

Functional groups

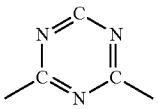

Other functional groups include but are not limited to sulfate ester, phosphate ester, thiol, imide, carbodiimide, imidazole, azide, azido, styrene, alkyl benzene, phenol, catechol, and the like.

Figure 4:
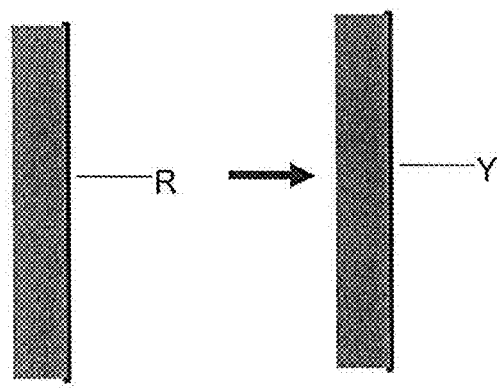
FIG. 4 is a representation of a group substitution reaction of an initial functional group, wherein the initial functional group is reacted to form a secondary functional group.

Another aspect of this invention includes a process for reacting the expanded functional TFE copolymer comprising pendant functional groups where at least some of the initial pendant functional groups that result from the polymerization process, form secondary functional groups that are different from the initial pendant functional groups as depicted in FIG. 4. In one embodiment, as depicted in FIG. 4, a group substitution is depicted as Y being substituted for the functional group R. Further reactions of the secondary functional groups are possible and in some embodiments, for example, may form tertiary functional groups on the expanded TFE copolymer material to further change the nature of an expanded functional TFE copolymer material, e.g. to obtain a desired chemical property.

The general formulae for comonomers of this invention are given in Table 1. The concentration of the comonomer containing a functional group in the resulting functional TFE copolymers may be less than 5 mol %, or less than 3 mol %, or less than 2 mol %, or less than 1 mol % or less than 0.5 mol %. The concentration of comonomer having a functional group in the resulting functional TFE copolymers may be greater than 0.015 mol %, greater than 0.04 mol %, greater than 0.07 mol %, greater than 0.1 mol %, greater than 0.5 mol %, greater than 1.0 mol %, greater than 2 mol %, or greater than 3 mol %.

The concentration of comonomer containing a functional group in the resulting functional TFE copolymers may be between 0.01 and 5 mol %, 0.01 and 3 mol %, or 0.01 and 2 mol %, and can be measured according to the methods described herein.

At least one functional comonomer may be polymerized with TFE to provide a copolymer having a multiplicity of pendant functional groups. More than one functional comonomer may also be provided. Where more than one functional comonomer is provided, the functional comonomers may provide the same or different functional groups that are pendant to the polymer chain. Additionally, one or more non-functional comonomers may be copolymerized with TFE and the at least one functional comonomer to form the expandable functional TFE copolymers having pendant functional groups. Non-functional comonomers are defined herein as comonomers that do not result in pendant functional groups on the polymer chain. Non-functional comonomers include but are not limited to fluoro-olefins i.e., hexafluoro-proylene (HFP), fluoro alkyl vinyl ethers; PMVE (perfluoromethyl vinyl ether), PEVE (perfluoroethyl vinyl ether) and PPVE (perfluoropropyl vinyl ether).

In one embodiment, a functional comonomer comprises a fluorovinyl ether of the general formula $$CF_2=CF-OR_fZ,$$

where $R_f$ represents a fluoro alkyl group optionally interrupted by one or more oxygen(s) and Z represents a functional group from Table 2. Z may be cyano or nitrile, aldehyde, carboxylic acid or salt, ester, amine, amide, carbonyl halide, sulfonyl halide, sulfonic acid or salts, sulfonamide, sulfonimide, anhydride, sulfide, phosphonic acid or salt, hydroxyl (alcohol), sulfate esters, phosphate esters, isocyanate, thiol, imide, carbodiimide, imidazole, azide, azido, styrene, alkyl benzene, phenol, catechol, and the like. Fluorovinyl ether monomers may include comonomers listed in Table 3.

TABLE 3

Fluoro Vinyl Ether Functional Comonomers

Cyano vinyl ethers $CF_2=CFOR_f-CN$
where $R_f$ is a fluorinated alkyl or alkyl ether group. Illustrative examples are:
$CF_2=CF-O(CF_2)_n-CN$
where $n = 2\text{-}12$, or preferably where $n = 2\text{-}6$;
$CF_2=CF-O[CF_2-CF(CF_3)-O]_n-CF_2-CF(CF_3)-CN$
where $n = 0\text{-}4$, or preferably where $n = 0\text{-}2$;
$CF_2=CF-[OCF_2CF(CF_3)]_x-O-(CF_2)_n-CN$
where $x = 1\text{-}2$, and $n = 1\text{-}4$; and
$CF_2=CF-O-(CF_2)_n-O-CF(CF_3)CN$
where $n = 2\text{-}4$. One preferred type of monomer includes perfluorinated polyethers having a nitrile group and a trifluorovinyl ether group, including perfluoro(8-cyano-5-methyl-3,6-dioxa-1-octene), $CF_2=CFOCF_2CF(CF_3)OCF_2CF_2CN$.

Sulfonyl fluoride vinyl ethers $CF_2=CFOR_fSO_2F$
where $R_f$ is a fluorinated alkyl or alkyl ether group. Illustrative examples are:
$CF_2=CFOCF_2CF_2SO_2F$ $CF_2=CFOCF_2CFOCF_2CF_2SO_2F$
                |
               $CF_3$ $CF_2=CFOCF_2CFOCF_2CFOCF_2CF_2SO_2F$
                |       |
              $CF_3$   $CF_3$ $CF_2=CFOCF_2CFOCF_2CF_2SO_2F$
                |
               $CF_2$
                |
                $O$
                |
               $CF_3$ One preferred sulfonyl fluoride-containing comonomer is perfluoro(3,6-dioxa-4-methyl-7-octane sulfonyl fluoride), $CF_2=CFOCF_2CFOCF_2CF_2SO_2F$
                |
               $CF_3$ Acid or ester vinyl ether or other acid precursors

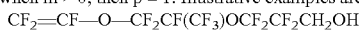

$CF_2=CF-[OCF_2CF(CF_3)]_m-O(CF_2)_n-(CH_2)_p OCOR$
where $R_f$ is a fluorinated alkyl or alkyl ether group;
$m = 0\text{-}20$; $n = 1\text{-}10$; $p = 1\text{-}4$; and R = alkyl. Illustrative examples are:
$CF_2=CF-[OCF_2CF(CF_3)]-O(OCF_2)_2-CH_2COOCH_3$
$CF_2=CFO(CF_2)_3CH_2COOCH_3$
$CF_2=CF-OCF_2CF(CF_3)OCF_2CF_2COOCH_3$
$CF_2=CFO(CF_2)_{1\text{-}8}COOCH_3$
$CF_2=CFO(CF_2)_{1\text{-}8}COOC_2H_5$
$CF_2=CFOCF_2CF(CF_3)OCF_2CF_2COOCH_3$ $$CF_2=CFO(CF_2)_{1\text{-}8}\overset{O}{\overset{\|}{P}}(OCH_3)_2$$

$CF_2=CF-[OCF_2CF(CF_3)]-OCF_2CF_2COOH$
$CF_2=CF-[OCF_2CF(CF_3)]-OCF_2CF_2CH_2OPO(OH)_2$
$CF_2=CF[OCF_2CF(CF_3)]-OCF_2CF_2CH_2-OCONH_2$

Hydroxyl vinyl ethers $CF_2=CF(OCF_2CFCF_3)_nO_p(CF_2)_mCH_2OH$
where $p = 0$ or 1; $m = 0\text{-}10$; $n = 1\text{-}20$; when m = 0, then p = 0,; and when m > 0, then p = 1. Illustrative examples are:
$CF_2=CF-O-CF_2CF(CF_3)OCF_2CF_2CH_2OH$ TABLE 3-continued Fluoro Vinyl Ether Functional Comonomers $CF_2=CFOCF_2CF_2CF_2CH_2OH$

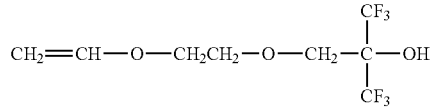

Other comonomers suitable for use in making TFE copolymers described herein include comonomers listed in Table 4.

TABLE 4

Other functional fluoro monomers $CF_2=CFSO_2F$
$CF_2=CFCF_2CF_2SO_2F$
$CF_2=CFCF_2OCF_2CF_2SO_2F$
$CF_2=CF(CF_2)_{0\text{-}8}COOCH_3$
$CF_2=CFCF_2OCF(CF_3)COOCH_3$
$CF_2=CFCF_2OCF(CF_3)CF_2OCF(CF_3)COOCH_3$
$CF_2=CFCF_2O(CF_2)_4COOCH_3$ The polymerization is carried out by an aqueous dispersion polymerization process to produce a fine powder resin, by modifying known processes (e.g., U.S. Pat. No. 4,016,345 to Holmes). The addition of the functional comonomer or optionally other comonomers to the reaction vessel is controlled. Sufficient dispersing agent is introduced into a water carrier where upon addition of TFE monomer in the presence of a suitable polymerization initiator, and upon agitation and under autogenous TFE pressure of 10-40 kg/cm², polymerization proceeds until the desired level of colloidally dispersed functional TFE copolymer particles is reached and the reaction is then stopped. The product of the polymerization reaction is the functional TFE copolymer dispersed within an aqueous colloidal dispersion.

In one embodiment, TFE monomer is pressurized into an autoclave containing water and polymerization initiators, along with paraffin wax to suppress coagulum formation, and an emulsifying agent. The addition of the functional comonomer or optionally other comonomers to the reaction is controlled. Where the comonomers are liquid, the process comprises emulsifying the comonomers prior to adding the comonomers to the reaction vessel. The comonomers are emulsified as emulsions in water containing a surfactant, preferably a fluoro surfactant.

Both the amount of functional comonomer added and the starting time of the comonomer addition, are determined based on the desired concentration of the comonomer in the resulting copolymer and the polymerization reactivity of the comonomer. The step of adding the comonomer, including the amount of comonomer added and the time in the polymerization batch cycle at which the comonomer is added, is controlled to assure that the comonomer is essentially completely reacted or consumed in the polymerization process before the polymerization is about 80-90% complete. The step of continuing polymerization, after essentially completely reacting or consuming the comonomer in the polymerization process, consists of polymerizing TFE for the final 10-20% of the polymerization in the absence of comonomer. This provides a functional TFE copolymer having high crystallinity of the material produced in the last 10-20% of the polymerization. The resulting functional TFE copolymer resin is paste extrudable and expandable into microporous structures.

In one embodiment, the process includes removing the comonomer prior to 80% to 90% completion of the polymerization, by for example, evacuating the comonomer at low pressure or by steam assisted distillation. Subsequently, the polymerization of TFE is resumed and completed.

After polymerization is complete, the process further comprises collecting the aqueous dispersion of particles which comprises the steps of lowering the temperature to about 20° C., removing it from wax, and removing it from the polymerization vessel. The aqueous dispersion is removed from the polymerization vessel, diluted with water and coagulated into fine powder by methods known in the art. The fine powder is dried in air or under vacuum at 100 to 200° C. prior to processing by paste extrusion and expansion.

In one embodiment a blend of functional expandable TFE copolymer may be comprised of a functional expandable TFE copolymer mixed with another TFE copolymer having a different concentration of functional comonomer, or different type of functional comonomer, or with a homopolymer of TFE or a modified TFE polymer. Expandable polymers suitable for blending with the functional expandable TFE copolymers include but are not limited to PTFE and polymers as described in U.S. Pat. No. 5,708,044 (Branca, 1998), U.S. Pat. No. 6,541,589 (Baillie, 2003), U.S. Pat. No. 7,531,611 (Sabol et al., 2009), U.S. patent application Ser. No. 11/906,877 (Ford), and the like.

In another embodiment the functional expandable TFE copolymer is blended with a melt processable perfluoropolymer or fluoropolymer, or any other polymer, or combinations thereof, through any conventional method including those taught in U.S. Pat. No. 6,127,486 to Burger et al. Other polymers that may be blended with the functional expandable TFE copolymers include but are not limited to FEP, PEA, PVDF, ionomers, fluoroelastomers, and the like.

The blend of polymers may be mixed through a co-coagulated process from dispersion, or blended in resin or fine powder form. The type and/or concentration of the components of the blend may be selected to provided desirable mechanical, functional or processing properties. For example, the components of a blend may be selected to provide a material that can be processed into a desired final material having desired functional and mechanical properties.

Filler material, such as carbon, silica, and the like, may also be combined with the functional expandable TFE copolymer through any conventional method including those as taught in U.S. Pat. No. 3,953,566 to Gore, U.S. Pat. No. 4,187,390 to Gore and U.S. Pat. No. 4,985,296 to Mortimer. In one embodiment, filler material is reacted with the pendent functional groups of the expandable TFE copolymer described herein. The filler material may be reacted prior to or after the expandable TFE copolymer is expanded.

Known paste-forming techniques can be used to convert the polymer resin to paste form into an article that can then be expanded after removing a lubricant. The steps in paste-forming processes include mixing the resin with a lubricant such as odorless mineral spirits and carrying out forming steps in which the resin is subject to shear.

The paste extrudable functional TFE copolymers made herein are expandable to microporous structures characterized by having nodes interconnected by fibrils, for example, by processes taught in U.S. Pat. No. 3,953,566 to make microporous expanded PTFE. Other processes for expanding the paste extruded resin include but are not limited to those methods that are described in commonly owned U.S. Pat. No. 4,902,423, to Bacino, U.S. Pat. No. 5,476,589 to Bacino, U.S. Pat. No. 5,814,405 to Branca et al., and U.S. Pat. No. 7,306,729 to Bacino et al.

In one embodiment a composite membrane comprises an expanded functional TFE copolymeric material having a microstructure characterized by nodes interconnected by fibrils wherein the copolymer is a TFE copolymer having functional groups pendant to the polymer chain, and another material imbibed at least partially thereto. The imbibed material may be a polymer, such as but not limited to an elastomer, or thermoplastic, or thermoset, or may include an organic material such as but not limited to biological material. In one embodiment the composite comprises an ion exchange material imbibed into the expanded material, such as taught in U.S. Pat. No. 6,254,978 to Behar et al. In some embodiments the imbibed material substantially occludes the pores of the expanded material as determined by the composite having a Gurley time of greater than 200 seconds, as measured using the method described herein. In another embodiment the imbibed material is imbibed throughout the thickness of the expanded TFE copolymer described herein. In yet another embodiment the imbibed material is reacted with the pendant functional groups of the expanded material. The imbibed material may be cross-linked with or covalently bonded to the pendant functional groups using standard cross-linking chemistries know in the art. For example, a perfluorinated sulfonyl fluoride resin can be reacted with ammonia or other amines to form a sulfonamide group. The sulfonamide groups can be crosslinked for example by exposure to elevated temperatures, to form sulfonimide groups.

Dense articles may be formed from expanded TFE copolymer materials according to the methods describing in commonly owned US Pub. No. 2008/0061472 to Kennedy et al.

In one embodiment, an expanded functional TFE copolymeric material is formed having a microstructure characterized by nodes interconnected by fibrils wherein the copolymer is a TFE copolymer, and wherein the comonomer comprises functional groups which, in the copolymer, are pendant to the polymer chain. The pendant functional groups can impart different properties to the TFE copolymers. Expanded functional TFE copolymers, and articles made therefrom, may undergo reactions such as chemical reactions with chemical reactants or reagents to react or change the functional groups to impart different chemical or physical properties to the expanded article. Reactants, include but are not limited to organic material, bioactive species, spacer arms, imbibed materials, filler materials, synthetic polymers, perfluoropolymers, fluoropolymers, ion exchange materials, elastomers, functional TFE copolymers described herein, and the like.

Another aspect of this invention includes a process for reacting the expanded functional TFE copolymer comprising pendant functional groups where at least some of the initial pendant functional groups that result from the polymerization process, form secondary functional groups that are different from the initial pendant functional groups, as depicted in FIG. 4. Further reactions of the secondary functional groups are possible and in some embodiments, for example, may form tertiary functional groups on the expanded TFE copolymer material to further change the nature of an expanded functional TFE copolymer material, e.g. to obtain a desired chemical property.

Organic and biochemistry reactions with the pendant functional groups described in Table 2 may include reactions between at least some of the initial pendant functional groups to form secondary functional groups. For example, in one embodiment, a crosslinking reaction comprising the reaction of an expanded functional TFE copolymer comprising three initial pendant nitrite groups (—CN) upon heating to a temperature above 250° C. forms a triazine structure resulting in crosslinking of the TFE copolymeric material.

In a further embodiment, at least some of the initial pendant functional groups are chemically reacted with another chemical to form secondary functional groups. For example, initial pendant functional groups such as amide functional groups, acid halide functional groups, and nitrite groups, are reacted with water to form acids as secondary functional groups, according to the following reactions.

—COOR+H₂O→—COOH where R is alkyl or fluoroalkyl;

—CONH₂+H₂O→—COOH;

—COX+H₂O→—COOH where X is halogen;

—SOOF+H₂O→—SOOOH; and

—CN+H₂O→—COOH

Additional chemical reactions include the reaction of initial pendant nitrite functional groups with ammonia to form amidine groups as secondary functional groups, for example by the following reaction.

—CN+NH₃→—C(=NH)NH₂

In one example an expanded functional TFE copolymer having pendant functional groups comprising an initial ester group can be reacted with other esters to form a secondary functional group in the form of a different ester group, according to the following reaction.

R₁—COOR+R₂—COOR'→R₁—COOR'+R₂—COOR where R₁ is the initial functional TFE copolymer for example, TFE-EVE (CF₂=CF—OCF₂CF(CF₃)OCF₂CF₂COOCH₃) copolymer, R is alkyl or fluoroalkyl group and R₂ is an alkyl or fluoroalkyl group and R' is an alkyl or fluoroalkyl group different than R.

In addition, the monomers listed in Table 2 can be reacted using methods that are well know in the art, including but not limited to transamidation, isocyanurate formation, uret formation, dehydrogenation and unsaturation formation, hydrolysis, aminolysis, condensation, electrophilic addition, nucleophilic substitution, elimination, hydrogen abstraction, Michael's addition, and the like.

Where the expanded functional TFE copolymer comprises pendant ester groups and/or pendant acid functional groups, the initial functional groups may be reacted with ammonia or other amines to form amide secondary functional groups, according to the following reactions.

—COOR+NH₃→—CONH₂

—COOH+NH₃→—CONH₂ where R is alkyl or fluoroalkyl.

Further, an expanded functional TFE copolymer comprising pendant nitrile initial functional groups can be reacted to reduce the nitrile groups to amine secondary functional groups according to the following reaction.

—CN→—CH₂—NH₂

In another embodiment wherein the expanded functional TFE copolymer comprises pendant sulfonyl fluoride initial functional groups that can be reacted with ammonia or other amines to form an expanded TFE copolymer comprising sulfonamide secondary functional groups, the expanded material can be further reacted to form sulfonimide tertiary functional groups upon heating as follows.

—SOOF+NH₃→—SO₂NH₂→—SO₂NHNSO₂—

In another embodiment, the functional TFE copolymer of the present invention may be treated with or exposed to radiation with or without the presence of other reactant to change existing functional groups or create new functional groups. In one embodiment the functional TFE copolymer material is exposed to radiation in the resin form and in another embodiment it is exposed in the expanded form.

The expanded microporous TFE copolymer material containing pendant functional groups provide good media for chemical reactions. Because the functional groups are from comonomers polymerized with TFE, the pendant functional groups are integrated and may be distributed throughout the microstructure of the expanded polymeric material. The pendant functional groups are surprisingly available for contact with each other or with additional chemical reagents, reactants, organic material, or bioactive species. Moreover, the non-functional part of the expanded microporous structure has high fluorine concentration (equal to or greater than 95 mol % TFE) which results in good chemical (solvent) resistance and stability at high temperatures which make the expanded functional copolymer material a good media for chemical reactions.

In a still further embodiment, the chemical reactants may include natural and synthetic chemicals that are able to react with pendant functional groups of the expanded functional TFE copolymers. Natural materials include biochemicals and biopolymers that include but are not limited to carbohydrates, carbohydrate polymers or polysaccharides, chitin, glycogen, heparin, heparan sulfate, polypeptides and proteins, collagen, gelatin, enzymes, nucleic acids, DNA, RNA, lipids, steroids, hormones, pharmaceuticals, and other therapeutic agents.

The reactants may also include synthetic polymers. For both natural or biopolymers and synthetic polymers, the reactive site of the reactant may also be a functional group that is pendant to the reactant polymer chain. The reactive site of the reactant may alternatively be a non-pendant group. Synthetic polymeric reactants include but are not limited to those listed in Table 5.

TABLE 5

Representative List of Synthetic Polymeric Reactants and Formulae

| | |
|---|---|
| TFE-PMVE-8CNVE copolymer | |
| —(CF₂—CF₂)—[CF₂—CF(OCF₃)]—CF₂—CFOCF₂CF(CF₃)OCF₂CF₂CN | |
| TFE-VDF-HFP-8CNVE copolymer | |
| —(CF₂—CF₂)—(CH₂—CF₂)—[CF₂—CF(CF₃)]—CF₂—CFOCF₂CF(CF₃)OCF₂CF₂CN | |
| Poly(vinyl acetate) | —[CH₂—CH(OCOCH₃)]— |
| Poly(vinyl alcohol) | —[CH₂CH(OH)]— |
| Poly(ethylene glycol) | HO—(CH₂—CH₂—O)ₙ—H |
| Poly(propylene glycol) | HO—(CH₂—CH₂—CH₂—O)ₙ—H |

TABLE 5-continued

Representative List of Synthetic Polymeric Reactants and Formulae

| | |
|---|---|
| Poly(ethylene imine) | —(CH$_2$—CH$_2$—NH)— |
| Poly(ethyl acrylate) | —[CH$_2$—CH(COOC$_2$H$_5$)]— |
| Poly(acrylic acid) | —[CH$_2$—CH(COOH)]— |
| Poly(acrylonitrile) | —[CH$_2$—CH(CN)]— |
| Poly(ethylene vinyl acetate) | —(CH$_2$—CH$_2$)$_m$—[CH$_2$—CH(OCOCH$_3$)]$_n$— |
| Poly(ethylene vinyl alcohol) | —(CH$_2$—CH$_2$)$_m$—[CH$_2$—CH(OH)]$_n$— |
| Poly(acrylamide) | —[CH$_2$—CH(CONH$_2$)]— |
| Poly(n-butyl isocyanate) | —[N(C$_4$H$_9$)—CO]— |
| Poly(dimethylsiloxane) | —[(CH$_3$)$_2$SiO]— |
| Poly(lactic acid) | —[O—CH(CH$_3$)—CO]— |
| Poly(methacrylonitrile) | —[CH$_2$—C(CH$_3$)(CN)]— |
| Poly(L-lactide) | —(CH$_2$—COO)— |

In one embodiment, where the synthetic polymer comprises an —OH group, such as in poly(vinyl alcohol) (PVA), the material may be esterified with a pendant functional —COOH group of the microporous expanded functional TFE copolymeric material to form ester bonds that connect the PVA and the microporous expanded material. In another embodiment, the pendant functional —COOH group may be preactivated for example, to an acylimidazole using carbonyldiimidazole, which may then be esterified with the PVA to form ester bonds that connect the PVA and the microporous expanded material.

In another embodiment, a —CN group of a terpolymer made from TFE, PMVE and 8-CNVE (i.e., see Table 5) may be reacted with a pendant functional —CN group of the microporous expanded functional TFE copolymer material to form triazine groups that crosslink the terpolymer with the microporous expanded material. In a further embodiment, fluoroelastomers that do not contain cyano functional groups may also be used to react with the pendant functional —CN group of the microporous expanded functional TFE copolymer material by adding triallylisocyanurate (TAlC) and peroxide to form crosslinking to improve the interface between the fluoroelastomer and the expanded microporous material.

Further, the expanded functional TFE copolymer may be reacted with biochemical materials such as heparin, a polysaccharide. For example, where the biochemical material comprises hydroxyl —OH, sulfonic acid —SOOOH and carboxylic acid —COOH functional groups, the —OH group may be reacted with pendant carboxylic acid on a microporous expanded functional TFE copolymer material to form an ester. The —OH groups may also react with an ester group on the microporous material to form a new ester group. The —SOOOH group may react with an amine group on the microporous expanded functional TFE copolymer material to form a sulfonamide or sulfonimide. The —COOH group on heparin may react with a pendant functional —OH group on the expanded microporous functional TFE copolymer material to form ester groups. A —COOH group from a biochemical material may also react with an amino group on the microporous expanded functional TFE copolymer material to form amide groups. A —CHO (aldehyde) group from a biochemical material may also react with an amino group on the microporous expanded functional TFE copolymer material to form imine groups. In one embodiment heparin is immobilized to the resin or expanded polymeric material described herein, and in some cases to the pendant functional group, by many methods including those taught in U.S. Pat. No. 6,461,665 to Scholander et al.

Figure 3:
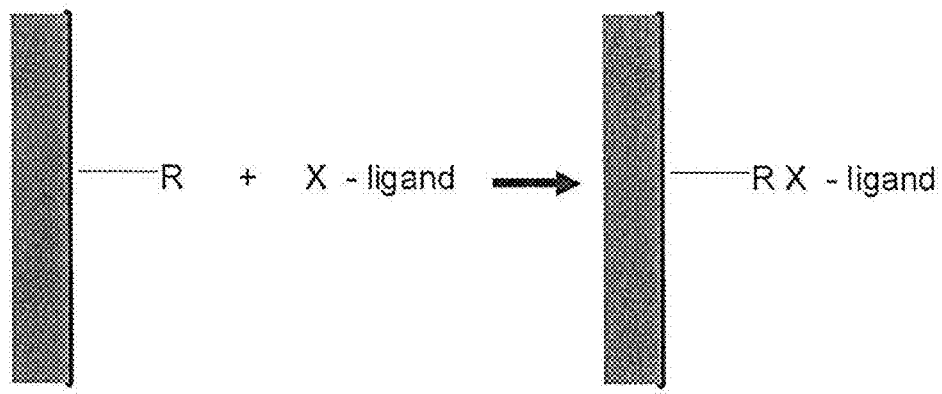
FIG. 3 is a representation of an immobilization of a bioactive species to a functional group.

A broad array of natural and synthetic bioactive species and other ligands such as biochemicals or biopolymers, and pharmaceutically or biologically active molecular compounds, or organic material can be reacted or otherwise immobilized to the functional group of a support member, as depicted in FIG. 3. A support member, as used herein refers to the functional TFE copolymer fine powder resin or expanded polymeric material comprising a functional TFE copolymer material as described herein. As used herein, the terms immobilize, attach, and their derivatives refer to adsorption, such as, physisorption or chemisorption, ligand/receptor interaction, covalent bonding, hydrogen bonding, or ionic bonding of a polymeric substance or a bioactive species to a support member. Bioactive species, as used herein, include enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, extracellular matrix material and/or its individual components, dyes and fluorescent probes, colloidal metals, pharmaceuticals, and therapeutics, for example. Cells, such as, mammalian cells, reptilian cells, amphibian cells, avian cells, insect cells, planktonic cells, cells from non-mammalian marine vertebrates and invertebrates, plant cells, microbial cells, protists, genetically engineered cells, and organelles, such as mitochondria, are also bioactive species. In addition, non-cellular biological entities, such as viruses, virenos, and prions are considered bioactive species. Natural and synthetic polymers are also considered bioactive species, and may be attached to the support member to alter surface energetics, hydrophilicity, hydrophobicity and lubricity; to resist to protein adsorption; to enhance affinity adsorption; and the like; examples of such polymers include but are not limited to those listed in Table 5, and also include but are not limited to polyethylene glycol, polypropylene glycol, hyaluronic acid, alginic acid, heparin, heparan sulfate, polyacrylamide, polyethyleneimine, dextran sulfate, cyclodextrin, agar, agarose, chitin, chitosan, polyvinylpyrrolidinone, polyvinyl alcohol, cellulose and its derivatives, starch polyaldehyde, polyhydroxyethyl methacrylate, silane and its derivatives, or another functional TFE copolymer as described herein, and the like.

Figure 5:
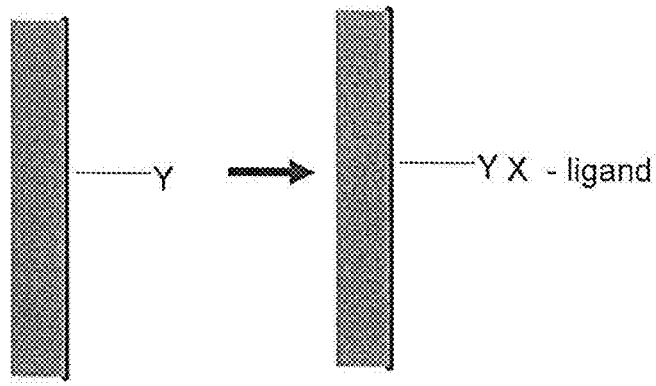
FIG. 5 is a representation of an immobilization of a bioactive species to a secondary functional group.
Figure 6:
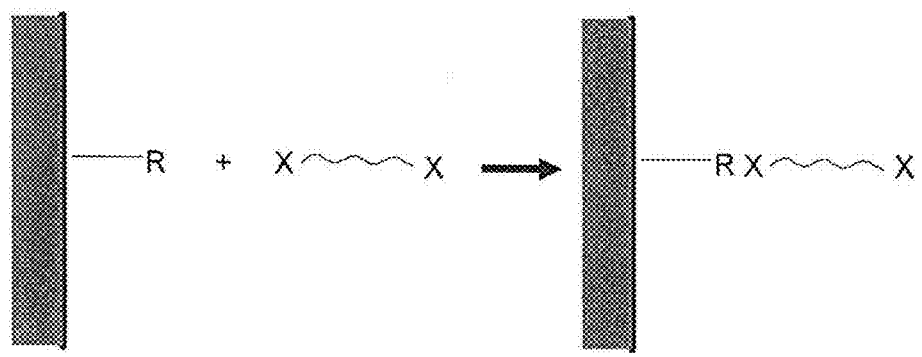
FIG. 6 is a representation of an immobilization of a spacer arm to a functional group.

A bioactive species may be immobilized to the functional TFE copolymer fine powder resin or expanded polymeric material comprising a functional TFE copolymer material as described herein, by any conventional method including those taught in U.S. Pat. No. 5,914,182 to Drumheller, U.S. Pat. No. 5,897,955 to Drumheller, U.S. Pat. No. 5,874,165 to Drumheller, U.S. Pat. No. 5,916,585 to Cook, et al. The bioactive species may be immobilized to the resin or expanded polymeric material as described herein without reaction to the pendant functional group, therein leaving the functional group available for other reactions. In one embodiment the bioactive species is immobilized to the resin or expanded polymeric material of the present invention through reaction directly to the pendant functional group, as depicted in FIG. 3. In another embodiment an initial functional group on the support member is converted to a second functional group different from the initial functional group as depicted in FIG. 4, and the bioactive species is immobilized to the second functional group as depicted in FIG. 5. In yet another embodiment the bioactive species is immobilized to the resin or expanded polymeric material of the present invention through an intermediate component that is attached to the pendant functional group. The intermediate component may comprise a covalent bond between the species and the support member, or may comprise a spacer arm. A spacer arm is immobilized onto the polymeric substrate in some cases, as depicted in FIG. 6, to enhance the yield of surface attachment, to minimize surface-induced steric effects, or to enhance receptor-ligand interactions. The spacer arm may be homobifunctional, homopolyfuntional, heterobifunctional, heteropolyfuntional, zero length, cleavable, photolytically labile, and the like. The spacer arm, in one embodiment, may also comprise a polymeric surfactant, or a multifunctional copolymer, comprised of at least one domain that has a physisorb or chemisorb affinity for the resin or expanded polymeric material of the present invention to allow physisorption or chemisorption of the multifunctional copolymer onto the surface of the resin or expanded polymeric material and at least one other domain that is chemically reactive to allow covalent immobilization of a bioactive species or allow cross-linking with a suitable cross-linking agent. The spacer arm may also comprise the functional expandable fluoropolymer having the function group listed in Table 2. The spacer arm may also comprise a first layer attached to the pendant functional group and a second layer attached to the first layer. The spacer arm of the first layer may be the same or different than the spacer arm of the second layer.

A wide range of intermediate components, including spacer arms, could be used as taught in U.S. Pat. No. 5,914, 182 to Drumheller, U.S. Pat. No. 5,897,955 to Drumheller, U.S. Pat. No. 5,874,165 to Drumheller, U.S. Pat. No. 5,916, 585 to Cook, et al.

Organic species including enzymes, cells and proteins, and spacer arms, may also be immobilized to the resin or expanded polymeric material as described herein and in some cases to the pendant functional group, by many methods including those taught in G T Hermanson, "Bioconjugate Techniques", 2nd Ed, Academic Press (Amsterdam), 2008, and specifically in chapter 1-8, 13-15, 17-18, 22-27, Methods in Enzymology, "Immobilized Enzymes and Cells", Part B, Vol 125, K. Mosbach (Ed), Academic Press (Orlando), 1987, and SS Wong, "Chemistry of Protein Conjugation and Cross-Linking", CRC Press (Boca Raton), 1993, specifically chapters 2-6 and 12.

The bioactive species in one embodiment is also a spacer arm including but not limited to those listed in Table 5, and including but not limited to polyalcohol such as polyvinyl alcohol; polyamine such as polyethylenemine; polyether such as polyethylene glycol, polyaldehyde such as starch polyaldehyde; polyester such as polyvinyl acetate; polycarboxylic acid such as polyacrylic acid; polyamide such as polyvinylpyrrolidinone, polyaryl ketone, polyazide, polythiol, polybiotin, polyavidin, polysilane, polydopamine, polyquinone, polysaccharide such as heparin, heparan sulfate, polyamino acid, polynucleic acid, polyalkane, and the like. The spacer arm may be homofunctional, heterofunctional, zero length, cleavable, photolytically labile, and the like. In another embodiment two or more bioactive species are immobilized to the resin or expanded polymeric material of the present invention and in some embodiments one is immobilized to the functional pendant group and the other is not. In another embodiment the polymeric material is a medical device. In another embodiment the polymeric material is a component of a medical device.

As used herein, the term medical device includes but is not limited to temporarily implantable materials and devices such as catheters, balloons, wound dressings, and the like; permanent implantables such as sutures, vascular grafts, stents, stent-grafts, patches, barriers, heart and vascular valves, tissue growth scaffolds, orthopedic devices, plugs, and the like, and non-implantables such as collection bags, dialysis medium, cell growth scaffolds, and the like. A medical device may also include ex vivo or in vitro materials and devices such as but not limited to tubing, membranes, chromatography medium, adsorption medium, affinity medium, bioseparation and biopurification medium, biofilters, substrates for protein & DNA analysis, and the like. A medical device may also include fabrics, garments, and the like to protect against disease or pathogen transmission and the like. A medical device may also be essentially any type of medical device, or a component of a medical device, that may be fabricated from the copolymers of the present invention.

TEST METHODS

Break Strength Test of Microporous ePTFE

A process for testing the break strength of a paste extruded and expanded functional microporous TFE copolymer beading is provided. The break strength associated with an extruded and expanded (stretched) TFE polymeric beading produced from a particular resin is directly related to that resin's general suitability for expansion, and various methods have been employed to measure break strength. The following procedure was used to produce and test expanded beading specimens made from the copolymers of this invention, the data for which are reported herein below.

For a given resin, 113.4 g of fine powder resin is blended together with 130 cc/lb (24.5 g) of Isopar® K. The blend is aged for about 2 hours at 22° C. in a constant temperature water bath. A 2.54 cm diameter cylindrical preform is made by applying about 1,860 kPa of preforming pressure for about 20 seconds. The preform is inspected to ensure it is crack free. An extruded beading is produced by extruding the preformed, lubricated resin through a 0.254 cm diameter die having a 30 degree included inlet angle. The extruder barrel is 2.54 cm in diameter and the ram rate of movement is 50.8 cm/min. The extruder barrel and die are at room temperature, maintained at 23° C., plus or minus 1.5° C. The Isopar® K is removed from the beading by drying it for about 25 minutes at 225-230° C. Approximately the first and last 2.5 m of the extruded beading are discarded to eliminate end effects. A 5.0 cm section of the extruded beading is expanded by stretching at 290° C. to a final length of 127 cm (expansion ratio of 25:1) and at an initial rate of stretch of 1000% per second, which is a constant rate of 50.8 cm per second. Approximately a 30 cm length from near the center of the expanded beading is removed, and the maximum break load of the removed sample held at room temperature (23° C. plus or minus 1.5° C.) is measured using an Instron® tensile tester using an initial sample length of 5.0 cm and a crosshead speed of 5.0 cm/min.

Measurements in duplicate are obtained and reported as the average value for the two samples. This procedure is similar to that described in U.S. Pat. No. 6,177,533B1.

Crystallinity Measurements of Expanded Membranes

Infrared spectra were obtained with a Nicolet 550 Series II spectrometer. The expanded membrane samples were used and scanned for 100 scans. The two peaks (about 2363 cm$^{-1}$ and 778 cm$^{-1}$) of interest were used for crystallinity measurements. The degree of crystallinity was calculated by using the following equation, Crystallinity %=100−(H$_{778}$/(H$_{2363}$×25))

where H$_{778}$ is the peak height near wavenumber 778 cm$^{-1}$ and H$_{2363}$ that near wavenumber 2363 cm$^{-1}$. The baseline for the peak near 778 cm$^{-1}$ was obtained from the line between 754 and 810 cm$^{-1}$. The baseline for the peak near 2363 cm$^{-1}$ was obtained from the line between 2200 and 2600 cm$^{-1}$.

Determination of Functional Groups

The Digilab FTS4000 infrared spectrometer was used to determine functional groups. FTIR spectra were obtained in the ATR mode by using a Pike Technologies MIRacle ATR with a Ge crystal. Wavenumbers for identifying specific functional groups are given in the examples below.

Determination of Compositions of Functional TFE Copolymers

NMR was used to quantify compositions of functional TFE copolymers. All NMR measurements were carried out on a Bruker BicSpin Avance II 300 MHz spectrometer operating at a resonance frequency of 282.4 MHz for fluorine-19 with a pulse duration of 3 μs. Spectra were collected at about 296 K on a Bruker-BioSpin 2.5 mm cross polarization magic angle spinning (CPMAS) probe positioned in a standard bore 7.05 T Bruker ultra shielded superconducting magnet. The samples were positioned at the magic angle and spun at 32.5 kHz. The sample weight for all experiments was about 10 to 25 mg. The software used for data acquisition and data processing was Topspin 1.3. The $^{19}$F chemical shifts were externally referenced to the CF$_2$ signal of PTFE at −123 ppm.

Thickness Measurements

Thickness was measured by placing the material between the two plates of a Kafer FZ1000/30 thickness snap gauge (Käfer Messuhrenfabrik GmbH, Villingen-Schwenningen, Germany). The average of the three measurements was used.

Density Measurements

Density was used to calculate the percent porosity of expanded materials using 2.2 g/cc as the full density of the sample. Samples die cut to form rectangular sections 2.54 cm by 15.24 cm were measured to determine their mass (using a Mettler-Toledo analytical balance model AG204) and their thickness (using a Kafer FZ1000/30 snap gauge). Using these data, density was calculated with the following formula:

$$\rho = \frac{m}{w * l * t}$$

in which: ρ=density (g/cc); m=mass (g); w=width (cm); l=length (cm); and t=thickness (cm). The average of the three measurements was used.

Tensile Break Load Measurements and Matrix Tensile Strength (MTS) Calculations

Tensile break load was measured using an INSTRON 1122 tensile test machine equipped with flat-faced grips and a 0.445 kN load cell. The gauge length was 5.08 cm and the cross-head speed was 50.8 cm/min. The sample dimensions were 2.54 cm by 15.24 cm. For longitudinal MTS measurements, the larger dimension of the sample was oriented in the machine, or "down web," direction. For the transverse MTS measurements, the larger dimension of the sample was oriented perpendicular to the machine direction, also known as the cross web direction. Each sample was weighed using a Mettler Toledo Scale Model AG204, then the thickness of the samples was taken using the Kafer FZ1000/30 thickness snap gauge. Three samples were then tested individually on the tensile tester. The average of the three maximum load (i.e., the peak force) measurements was used. The longitudinal and transverse MTS were calculated using the following equation:

MTS=(maximum load/cross-section area)*(density of PTFE)/density of the sample), wherein the density of PTFE is taken to be 2.2 g/cc.

Bubble Point Measurements

The bubble point and mean flow pore size were measured according to the general teachings of ASTM F31 6-03 using a Capillary Flow Porometer (Model CFP 1500 AEXL from Porous Materials Inc., Ithaca, N.Y.). The sample membrane was placed into the sample chamber and wet with SilWick Silicone Fluid (available from Porous Materials Inc.) having a surface tension of 19.1 dynes/cm. The bottom clamp of the sample chamber had a 2.54 cm diameter, 3.175 mm thick porous metal disc insert (Mott Metallurgical, Farmington, Conn., 40 micron porous metal disk) and the top clamp of the sample chamber had a 3.175 mm diameter hole. Using the Capwin software version 6.62.1 the following parameters were set as specified in the table below. The values presented for bubble point and mean flow pore size were the average of two measurements.

| Parameter | Set Point |
| --- | --- |
| maxflow (cc/m) | 200000 |
| bublflow (cc/m) | 100 |
| F/PT (old bubltime) | 40 |
| minbppres (PSI) | 0 |
| zerotime (sec) | 1 |
| v2incr (cts) | 10 |
| preginc (cts) | 1 |
| pulse delay (sec) | 2 |
| maxpre (PSI) | 500 |
| pulse width (sec) | 0.2 |
| mineqtime (sec) | 30 |
| presslew (cts) | 10 |
| flowslew (cts) | 50 |
| eqiter | 3 |
| aveiter | 20 |
| maxpdif (PSI) | 0.1 |
| maxfdif (cc/m) | 50 |
| sartp (PSI) | 1 |
| sartf (cc/m) | 500 |

Gurley Measurements

The Gurley air flow test measures the time in seconds for 100 cm$^3$ of air to flow through a 6.45 cm$^2$ sample at 12.4 cm of water pressure. The samples were measured in a Gurley Densometer Model 4340 Automatic Densometer. The average of the three measurements was used.

The following examples are intended to be illustrative of the invention, but are not to be construed as limiting the scope of the invention in any way.

EXAMPLE 1

A fine powder resin comprising the copolymer of TFE and 8-CNVE was prepared as follows.

To a 50-liter, horizontal polymerization reactor equipped with a 3-bladed agitator was added 1.5 kg of paraffin wax, 28 kg of de-ionized (DI) water, 18 g of ammonium perfluorooctanoic acid (APFO) and 5 g of succinic acid dissolved in about 50 g of DI water. The reactor and contents were heated above the melting point of the wax. The reactor was repeatedly vacuumed and pressurized (to about 1 atmosphere or less) with TFE until the oxygen level was reduced to 20 ppm or less. The contents were briefly agitated at about 60 rpm between vacuum and purge cycles to ensure that the water was deoxygenated. 35 g of perfluoro(8-cyano-5-methyl-3,6-dioxa-1-octene) (8-CNVE) ($CF_2$=$CFOCF_2CF(CF_3)OCF_2CF_2CN$), 5 g of 20% APFO, 250 g of DI water were emulsified by Omni Mixer Homogenizer. To the reactor under vacuum was added the above 8-CNVE emulsion as a precharge of comonomer, and the reactor was heated to 83° C. TFE was then added to the reactor until the pressure reached 2.8 MPa, and $KMnO_4$ in DI water solution (0.063 g/L) was injected at 80 ml/min. until about 4 kg of TFE had been added. This was accomplished in about 64 minutes. About 320 ml of 20% APFO solution was added in 40 ml increments, the first increment being added after about 1 kg of TFE had been added to the reactor, and the subsequent increments added after each subsequent 1 kg of TFE had been added, so that the final increment was added after 9 kg of TFE had been charged. The $KMnO_4$ addition rate was decreased to 40 ml/min at the 4 kg TFE level and continued at this rate until about 6 kg of TFE had been added, at which time the addition of $KMnO_4$ was stopped.

The polymerization reaction was then allowed to continue and the reaction was stopped after about 16 kg of TFE had been added to the reactor. The weight of the dispersion produced was 49.9 kg, and the solid content of the dispersion was 32.1 wt %. The raw dispersion particle size (RDPS) of the polymer particles was 0.175 micron.

The polymer dispersion was diluted to about 15 wt % with DI water and then coagulated with diluted nitric acid (300 ml 65% nitric acid diluted with 700 ml DI water) at about 16° C. The ratio of the diluted polymer dispersion to nitric acid was 20 kg dispersion per 100 ml diluted nitric acid. The agitation speed for coagulation was about 275 rpm. The coagulum was dried at 130° C. for 18 hours under vacuum. Solid-state $^{19}F$ NMR was carried out to characterize the composition of the polymer. This polymer contains 0.017 mol % (0.064 wt %) 8-CNVE. The break strength of the beading was approximately 42 newtons (N).

EXAMPLE 2

A fine powder resin comprising the copolymer of TFE and 8-CNVE was prepared as follows.

The procedures for Example 1 were repeated except that the concentration of the $KMnO_4$ solution was 0.1 g/L. The $KMnO_4$ solution was injected at 80 ml/mm. until about 4 kg of TFE had been added. This was accomplished in about 38 minutes. Then the $KMnO_4$ addition rate was decreased to 40 ml/min and continued at this rate until about 6 kg of TFE had been added, at which time the addition of $KMnO_4$ was stopped. The total addition time of $KMnO_4$ solution was about 43 minutes.

The polymerization reaction was then allowed to continue and the reaction was stopped after about 16 kg of TFE had been added to the reactor. The weight of the dispersion produced was 49.2 kg, and the solid content of the dispersion was 34.5 wt %. The raw dispersion particle size (RDPS) of the polymer particles was 0.208 micron.

The dispersion was coagulated in the same process as described in Example 1 and dried at 130° C. for 18 hours under vacuum. Solid-state $^{19}F$ NMR was carried out to characterize the composition of the polymer. This polymer contains 0.019 mol % (0.072) wt % 8-CNVE.

EXAMPLE 3

A fine powder resin comprising the copolymer of TFE and 8-CNVE was prepared as follows.

The procedures for Example 1 were repeated except that 52 g 8-CNVE was added to 5 g of 20% APFO and 250 g of DI water, emulsified by Omni Mixer Homogenizer, and added as a precharge to the reaction. The concentration of the $KMnO_4$ solution was 0.1 g/L. The $KMnO_4$ solution was injected at 80 ml/min until about 3 kg of TFE had been added. This was accomplished in about 63 minutes. Then the $KMnO_4$ addition rate was decreased to 40 ml/min and continued at this rate until about 4 kg of TFE had been added. The $KMnO_4$ addition rate was again increased to 80 ml/min and continued at this rate until about 6 kg of TFE had been added, at which time the addition of $KMnO_4$ was stopped. The total addition time of $KMnO_4$ solution was about 86 minutes.

The polymerization reaction was then allowed to continue and the reaction was stopped after about 16 kg of TFE had been added to the reactor. The weight of the dispersion produced was 52.2 kg, and the solid content of the dispersion was 32.8 wt %. The raw dispersion particle size (RDPS) of the polymer particles was 0.186 micron.

The dispersion was coagulated in the same process as described in Example 1 and dried at 130° C. for 18 hours under vacuum. Solid-state $^{19}F$ NMR was carried out to characterize the composition of the polymer. This polymer contains 0.044 mol % (0.17 wt %) 8-CNVE. The break strength of the beading was 45N.

EXAMPLE 4

A fine powder resin comprising the copolymer of TFE and 8-CNVE was prepared as follows.

The procedures for Example 1 were substantially repeated except that 118 g 8-CNVE was added to 5 g of 20% APFO and 250 g of DI water, emulsified by Omni Mixer Homogenizer, and added as a precharge to the reaction. The concentration of the $KMnO_4$ solution was 0.15 g/L. The $KMnO_4$ solution was injected at 80 ml/min until about 2 kg of TFE had been added, at which time the addition of $KMnO_4$ was stopped. The total addition time of $KMnO_4$ solution was about 143 minutes. 10.4 kg of $KMnO_4$ solution was added.

The polymerization reaction was then allowed to continue and the reaction was stopped after about 13.4 kg of TFE had been added to the reactor. The weight of the dispersion produced was 52.8 kg, and the solid content of the dispersion was 27.9 wt %. The raw dispersion particle size (RDPS) of the polymer particles was 0.194 micron.

The dispersion was coagulated in the same process as described in Example 1 and dried at 130° C. for 18 hours under vacuum. Solid-state $^{19}F$ NMR was carried out to characterize the composition of the polymer. This polymer contains 0.13 mol % (0.51 wt %) 8-CNVE. The break strength of the beading was 47N.

EXAMPLE 5

A fine powder resin comprising the copolymer of TFE and PSVE was prepared as follows.

To a 50-liter, horizontal polymerization reactor equipped with a 3-bladed agitator was added 1.5 kg of paraffin wax and 28 kg of DI water, 18 g of APFO and 5 g of succinic acid dissolved in about 50 g of DI water. The reactor and contents were heated above the melting point of the wax. The reactor was repeatedly vacuumed and pressurized (to about 1 atmosphere or less) with TFE until the oxygen level was reduced to 20 ppm or less. The contents were briefly agitated at about 60 rpm between vacuum and purge cycles to ensure that the water was deoxygenated. 1500 g of perfluoro(8-sulfonic acid fluoride-5-methyl-3,6-dioxa-1-octene) (PSVE)

($CF_2$=CFOCF$_2$—CF(CF$_3$)OCF$_2$CF$_2$SOOF), 50 g of 20% APFO, and 1500 g of DI water were emulsified by Omni Mixer Homogenizer. To the reactor under vacuum 688 g of the above PSVE emulsion was added as a precharge of comonomer, and the reactor was heated to 83° C. TFE was then added to the reactor until the pressure reached 2.8 MPa, and KMnO$_4$ in DI water solution (0.063 g/L) was injected at 80 ml/min. until about 4 kg of TFE had been added. A drop in pressure indicated the start of polymerization. TFE was continuously added to maintain the pressure. About 320 ml of 20% APFO solution was mixed with the rest of the PSVE solution. The mixed solution was added with an increment of 43 ml for 200 g of TFE consumed. The first increment was added after about 200 g of TFE had been added to the reactor, and the subsequent increments were added after each subsequent 200 g of TFE had been added. The final increment was added after 12 kg of TFE had been charged. The KMnO$_4$ addition rate was decreased to 40 ml/min at the 4 kg TFE level and continued at this rate until about 10 kg of TFE had been added, at which time the addition of KMnO$_4$ was stopped. This was accomplished in about 47 minutes.

The polymerization reaction was then allowed to continue and the reaction was stopped after about 16 kg of TFE had been added to the reactor. The weight of the dispersion produced was 50.5 kg, and the solid content of the dispersion was 36.6 wt %. The raw dispersion particle size (RDPS) of the polymer particles was 0.270 micron.

The dispersion was coagulated in the same process as described in Example 1 and dried at 130° C. for 18 hours under vacuum. Solid-state $^{19}$F NMR was carried out to characterize the composition of the polymer. This polymer contains 1.9 mol % (8.0 wt %) PSVE. The break strength of the beading was 28.5 N.

EXAMPLE 6

A fine powder resin comprising the copolymer of TFE and EVE was prepared as follows.

To a 50-liter, horizontal polymerization reactor equipped with a 3-bladed agitator was added 1.5 kg of paraffin wax, 28 kg of DI water, 18 g of APFO and 5 g of oxalic acid dissolved in about 50 g of Di water. The reactor and contents were heated above the melting point of the wax. The reactor was repeatedly vacuumed and pressurized (to about 1 atmosphere or less) with TFE until the oxygen level was reduced to 20 ppm or less. The contents were briefly agitated at about 60 rpm between vacuum and purge cycles to ensure that the water was deoxygenated. 80 g of perfluoro(8-carboxymethyl-5-methyl-3,6-dioxa-1-octene) (EVE) ($CF_2$=CF—OCF$_2$CF(CF$_3$)OCF$_2$CF$_2$COOCH$_3$), 5 g of 20% APFO, and 250 g of DI water were emulsified by Omni Mixer Homogenizer. To the reactor under vacuum was added the above EVE emulsion as a precharge of comonomer, and the reactor was heated to 83° C. TFE was then added to the reactor until the pressure reached 2.8 MPa, and KMnO$_4$ in DI water solution (0.15 g/L) was injected at 80 ml/min until about 1 kg of TFE had been added. A pressure drop indicated that polymerization started. TFE was continuously added to maintain the pressure. After 1 kg of TFE was added, the injection rate of KMnO$_4$ in DI water solution was decreased to 40 ml/min until 3 kg of TFE had been added and then the solution was injected at 20 ml/min. Until about 6 kg of TFE had been added, at which time the addition of KMnO$_4$ was stopped. This was accomplished in about 15 minutes. About 320 ml of 20% APFO solution was added in 40 ml increments, the first increment being added after about 2 kg of TFE had been added to the reactor, and the subsequent increments were added after each subsequent 1 kg of TFE had been added, so that the final increment was added after 9 kg of TFE had been charged.

The polymerization reaction was then allowed to continue and the reaction was stopped after about 16 kg of TFE had been added to the reactor. The weight of the dispersion produced was 45.6 kg, and the solid content of the dispersion was 35.1 wt %. The raw dispersion particle size (RDPS) of the polymer particles was 0.232 micron.

The dispersion was coagulated in the same process as described in Example 1 and dried at 180° C. for 18 hours under vacuum. Solid-state $^{19}$F NMR was carried out to characterize the composition of the polymer. This polymer contains 0.098 mol % (0.41 wt %) EVE. The break strength of the beading was 23.6 N.

EXAMPLE 7

A fine powder resin comprising the copolymer of TFE and EVE was prepared as follows.

The procedures for Example 6 were substantially repeated except that the reactor was evacuated after 10 kg of TFE had been added into the reactor and then TFE was recharged into the reactor until the pressure of the reactor was 2.8 MPa. Then, the KMnO$_4$ solution was injected at 80 ml/min. until about 1 kg of TFE had been added. Then the KMnO$_4$ addition rate was decreased to 40 ml/min and after 2 kg of TFE was added, the KMnO$_4$ injection rate was decreased to 20 ml/min until 6 kg of TFE had been added, at which time the addition of KMnO$_4$ was stopped. The total addition time of KMnO$_4$ solution was about 31 minutes.

The polymerization reaction was then allowed to continue and the reaction was stopped after about 16 kg of TFE had been added to the reactor. The weight of the dispersion produced was 46.2 kg, and the solid content of the dispersion was 35.4 wt %. The raw dispersion particle size (RDPS) of the polymer particles was 0.238 micron.

The dispersion was coagulated in the same process as described in Example 1 and dried at 180° C. for 18 hours under vacuum. Solid-state $^{19}$F NMR was carried out to characterize the composition of the polymer. This polymer contains 0.095 mol % (0.40 wt %) EVE. The break strength of the beading was 28.0 N.

EXAMPLE 8

An expanded functional copolymer comprising the copolymer of TFE and 8-CNVE was prepared as follows.

The resin from Example 3 was mixed with Isopar® K (Exxon Mobil Corp., Fairfax, Va.) at a concentration of 0.217 g/g of resin and formed into a pellet approximately 10 cm in diameter at a pressure of about 2070 kPa. The pellet was heated to about 50° C. and paste extruded into a tape having dimensions of about 0.076 cm thick and about 15.25 cm wide through a die having a reduction ratio of about 100 to 1, at a average extrusion pressure of about 10,300 kPa. The reduction ratio is the ratio of the cross sectional area of the extruder barrel to the cross sectional area of the extrusion die exit. The resultant tape was calendared at a rate of 50 meters/minute at about 45° C. to about 0.020 cm thick and about 15.25 cm wide. The lubricant was removed by heating at 180° C. to 210° C. The width of the dried tape was about 14.6 cm.

The resultant tape was stretched in the longitudinal direction at about 300° C. and 4.5 meters/minute to a ratio of 10:1. The resultant tape was about 8.9 cm wide. The resultant tape was stretched transversely at 300° C. at 19.8 meters/minute at a ratio of 7.5:1 and sintered at about 390° C. for about 20 seconds. The resultant membrane was characterized and the results are given in Table 6. A scanning electron micrograph, at 10,000 magnification, of the membrane is given in FIG. 1.

TABLE 6

Properties of Membrane Made in Example 8

|  | Example 8 (fine powder produced in Example 3) |
|---|---|
| Porosity (%) | 85 |
| Mean Flow Pore size (μm) | 0.16 |
| Thickness (μm) | 2.5 |
| Density (g/cc) | 0.39 |
| Crystallinity (%) | 71 |
| Avg. Matrix Tensile Strength (MPa) | 230 |

EXAMPLE 9

An expanded functional copolymer comprising the copolymer of TFE and PSVE was prepared as follows.

Figure 2:
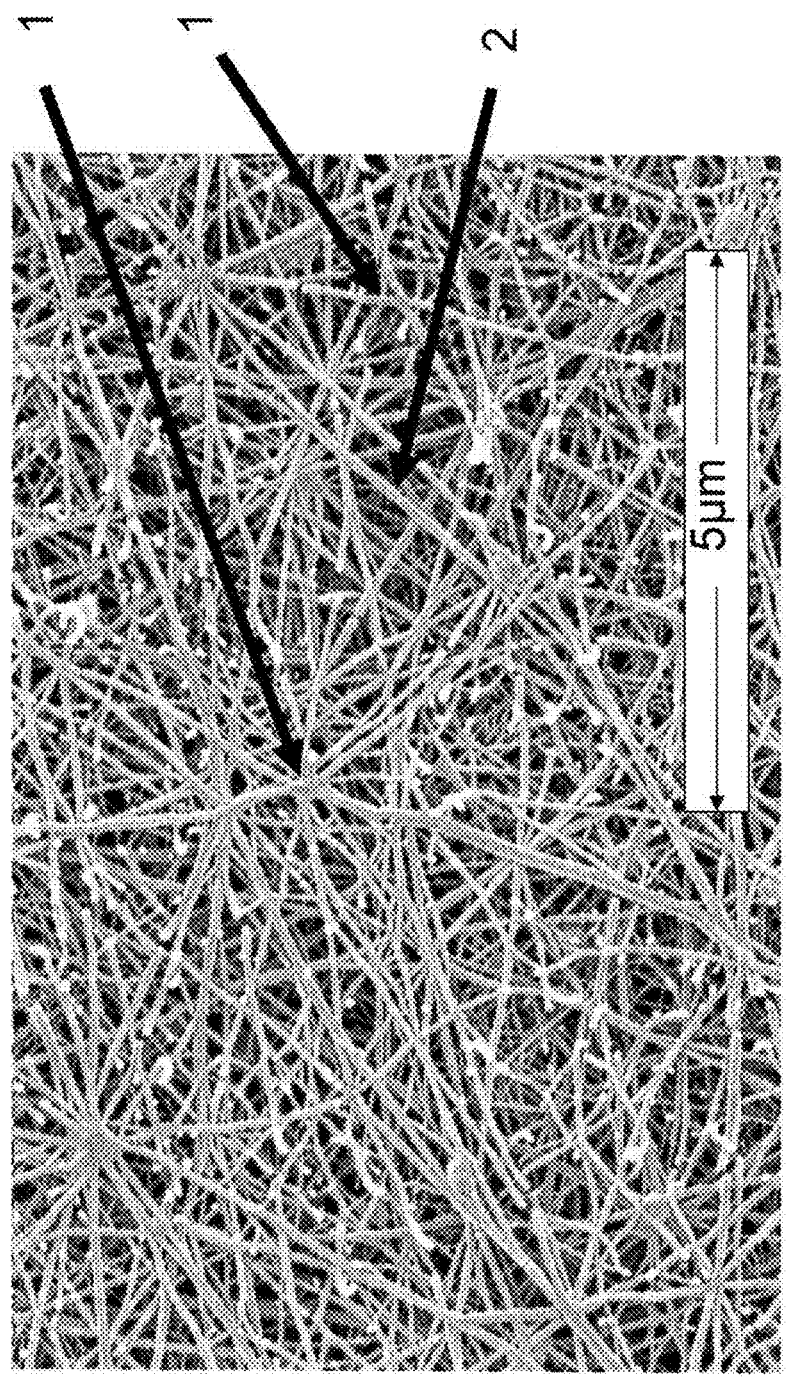
FIG. 2 SEM photomicrograph of an expanded sheet of functional TFE copolymer taken at 10,000× magnification.

A resin made in accordance with Example 5 containing 0.76 mol % (3.3 wt %) PSVE was both paste extruded into a tape and stretched in accordance with the processes of Example 8 except that the lubricant was removed by heating at about 250° C. The extruded tape had a width of about 13 cm and then the tape was paste stretched into a microporous membrane. The resultant membrane was characterized and the results are given in Table 7. A scanning electron micrograph, at 10,000 magnification, of the membrane is given in FIG. 2.

TABLE 7

Properties of Membrane Made in Example 9

|  | Example 9 |
|---|---|
| Mass/area (g/m$^2$) | 4.1 |
| Thickness (μm) | 2.5 |
| Gurley (sec) | 9.6 |
| Bubble Point (kPa) | 630 |
| Avg Matrix Tensile Strength (MPa) | 230 |

EXAMPLE 10

An expanded functional copolymer comprising the copolymer of TFE and 8-CNVE was reacted as follows.

An expanded microporous functional TFE copolymer membrane was made according to Example 8, from a PTFE fine powder prepared according to the process described in Example 3 containing 0.044 mol % (0.17 wt %) 8CNVE. The expansion process, carried out at about 300° C. and then restrained and heated at about 390° C. in an oven for about 20 seconds, resulted in an expanded microporous membrane containing triazine (about 1560 cm$^{-1}$), a crosslinked structure, and the unreacted cyano group (about 2297 cm$^{-1}$) determined by FTIR.

EXAMPLE 11

An expanded functional copolymer comprising the copolymer of TFE and 8-CNVE was reacted as follows.

Aminopropyltriethoxysilane (Aldrich) was mixed with a 95 wt % ethanol (Aldrich)/5 wt % DI water solution to yield a 10 wt % silane solution. About five minutes were allowed for hydrolysis and forming the silanol groups. An expanded functional TFE copolymer membrane made according, to Example 8 from a TFE copolymer fine powder containing 0.044 mol % (0.17 wt %) 8-CNVE was immersed in the solution for 2 minutes. It was then rinsed free of excess silane solution by dipping briefly in ethanol and air dried. Curing of the membrane was carried out at 110° C. for 30 min. The reacted membrane became transparent in water, indicating it was hydrophilic. The unreacted membrane was white in water, indicating it was hydrophobic. A hydrophilic membrane as described herein will exhibit water penetration into the pores of the expanded membrane after exposure to water, including surface exposure to water or submerging in water.

EXAMPLE 12

An expanded functional copolymer comprising the copolymer of TFE and 8-CNVE was reacted as follows.

An expanded functional TFE copolymer membrane made according to Example 8 from a TFE copolymer fine powder containing 0.044 mol % (0.17 wt %) 8-CNVE prepared in Example 3 was first wetted with isopropanol (IPA) (Aldrich) and then immersed in a 28 wt % aqueous ammonium hydroxide solution (Aldrich) at room temperature for 20 hours. It was then rinsed with DI water and air dried. The reacted expanded functional TFE copolymer membrane contains a new group, amidine (about 1743 cm$^{-1}$), determined by FTIR.

EXAMPLE 13

An expanded functional copolymer comprising the copolymer of TFE and 8-CNVE was cross linked with a fluoroelastomer.

Viton™ GF-S (fluoroelastomer) was compounded with 4 phr triallylisocyanurate (Aldrich) and 4 phr Luperox™ 101 (Aldrich) on a mill; the compounded mixture was dissolved in MEK (methyl ethyl ketone) to form a 20% solids solution. An expanded functional TFE copolymer membrane was made according to Example 8 from a TFE copolymer fine powder made according to the process of Example 3 containing 0.044 mol % (0.17 wt %) 8-CNVE. The membrane was imbibed with the Viton™ compound and dried at 90° C. Slabs (composite A) having a thickness of about 0.5 to 0.76 mm were made by stacking Viton™ imbibed expanded functional TFE copolymer membrane. Expanded functional TFE copolymer/Viton™ composite was formed by molding at 180° C. for 10 min followed by post-curing in a convection oven at 233° C. for 24 hours. Comparative slabs (composite B) were made by a similar process, except that ePTFE membrane was used in place of expanded functional TFE copolymer membrane and therefore, did not contain 8-CNVE. The IMASS peel tester was used for peel tests that were carried out in the T-peel mode with a 5-lb load cell at a speed of 6 in/min. Peel strengths were 2.2 and 1.5 lb/in for composite A and composite B, respectively.

EXAMPLE 14

An expanded functional copolymer comprising the copolymer of TFE and PSVE was reacted as follows.

An expanded functional TFE copolymer membrane made by the processing conditions of Example 9, was made from a functional TFE copolymer fine powder containing 1.9 mol % (8.0 wt %) PSVE made according to the process of Example 5. The membrane was first wetted with IPA and then immersed in a 20 wt % KOH solution (Aldrich) at 100° C. for 24 hours. It was then rinsed with DI water and was immersed in 15 wt % nitric acid (Aldrich) at 60° C. for 24 hours. The reacted membrane was rinsed with DI water and dried at 100° C. for 1 hour. The conversion of the sulfonyl fluoride group (about 1469 cm$^{-1}$) into the sulfonic acid group (about 1059 cm$^{-1}$) was confirmed by FTIR.

EXAMPLE 15

An expanded functional copolymer comprising the copolymer of TFE and PSVE was reacted as follows.

An expanded functional TFE copolymer membrane made by the processing conditions of Example 9, was made from a functional TFE fine powder containing 1.9 mol % (8.0 wt %) PSVE made according to the process of Example 5. The membrane was first wetted with IPA and then immersed in a 28 wt % aqueous ammonium hydroxide solution at about 5° C. for 3 hours. The reacted membrane was rinsed with DI water and air dried. The expanded functional TFE copolymer membrane was cured by heating at 200° C. for 1 hour. The sulfonimide group (about 1740 cm$^{-1}$) the crosslinked structure, was determined by FTIR.

EXAMPLE 16

An expanded functional copolymer comprising the copolymer of TFE and EVE was reacted as follows.

Expanded functional TFE copolymer membrane was made from fine powder made according to the process of Example 6. This fine powder contained 0.098 mol % (0.41 wt %) EVE.

The resin from Example 6 was mixed with Isopar® K (Exxon Mobil Corp., Fairfax, Va.) at a concentration of 0.207 g/g of resin and formed into a pellet approximately 10 cm in diameter at a pressure of about 2070 kPa. The pellet was heated to about 50° C. and paste extruded into a tape having dimensions of about 0.076 cm thick and about 15.25 cm wide through a die having a reduction ratio of about 100 to 1, at an average extrusion pressure of about 15,000 kPa. The reduction ratio is the ratio of the cross sectional area of the extruder barrel to the cross sectional area of the extrusion die exit. The resultant tape was calendared at a rate of 8.2 meters/minute at about 45° C. to about 0.015 cm thick. The lubricant was removed by heating at 180° C. to 210° C. The width of the dried tape was about 15.8 cm.

The resultant tape was stretched in the longitudinal direction at about 250° C. and 15.24 meters/minute to a ratio of 2:1. The resultant tape was about 13.5 cm wide. The resultant tape was stretched transversely at 300° C. at 100% per second at a ratio of 6:1 in the transverse direction.

The membrane was first wetted with isopropyl alcohol and then immersed in a 28 wt % aqueous ammonium hydroxide solution at about 5° C. for three hours. The reacted membrane was rinsed with DI water and air dried at room temperature. The reacted membrane became semi transparent in water indicating it was hydrophilic. The unreacted membrane was white in water, indicating it was hydrophobic.

EXAMPLE 17

An expanded functional copolymer comprising the copolymer of TFE and EVE was reacted as follows.

Expanded functional TFE copolymer was made according to Example 6. This fine powder contained 0.098 mol % (0.41 wt %) EVE. The fine powder was processed to a membrane according to the processes of Example 16.

The membrane was first wetted with isopropyl alcohol. The pre-wetted expanded TFE copolymer membrane was immersed in 50 wt % aqueous sulfuric acid and held at 60° C. for 24 hours. The membrane was then rinsed with DI water and dried at 60° C. for 2 hours. FTIR spectra showed the presence of the carboxylic acid (about 3300 cm$^{-1}$) functionality, showing at least some of the ester functional group was hydrolyzed to the carboxylic acid.

EXAMPLE 18

An imbibed composite was prepared as follows.

An expanded functional TFE copolymer membrane made according to the process as described in Example 9 was made from a functional TFE copolymer fine powder containing 1.8 mol % (7.7 wt %) PSVE made according to Example 5. The expanded material had a mass per area of 5.2 g/m$^2$. A solution of TFE-PSVE ionomer, having approximately 18 mol % PSVE, was prepared according to the teachings of Wu et. al. [US 2008/007036] in Paragraphs 113-114 and then diluted with ethanol and DI water to 13.2% wt % solids in a 13.2% water/73.8% wt % ethanol solution. This ion exchange material solution was coated on a FLUOROJU™ film (Mitsubishi Plastics, Inc) placed onto a glass plate. The coating was done using a draw down blade with a coating gap of 7 mil (178 microns). The composite membrane was then stretched over the wet coating and allowed to infiltrate. After infiltration, it was dried for 20-60 seconds with a hair drier. Then, a second coating of the same ion exchange material solution was done using a 1.5 mil (38 microns) gap. The second coating was then also dried with a hair drier for 20-60 seconds. This imbibed composite membrane on the FLUOROJU™ film on the glass plate was placed in an air furnace at 160° F. for 3 minutes and then removed to cool. The imbibed composite membrane was then removed from the FLUOROJU™ film backer. The final measured thickness of this imbibed composite membrane was 12±2 microns. This material was subsequently tested as a solid polymer electrolyte in a fuel cell by first forming a Membrane Electrode Assembly (MEA) using standard processes such as those described in US 2007/007206, paragraph 121. This MEA was subsequently tested using standard fuel cell test protocols such as those described in US 2007/007206. A polarization curve was successfully obtained indicating the imbibed composite membrane was acting as a solid polymer electrolyte.

EXAMPLE 19

An inventive solid polymer electrolyte membrane was prepared using the process described in Example 18 using a starting expanded membrane with a mass per unit area of 5.2 g/m$^2$, except that in this example the initial coating draw down gap was 5 mil (125 microns) and the second draw down gap was 3 mil (75 microns). The final measured thickness of this imbibed composite membrane was 12±2 microns. The measured Gurley of this sample was greater than 200 seconds. Further testing showed the Gurley was greater than 1000 seconds, and greater than 5000 seconds, and greater than 10,000 seconds.

EXAMPLE 20

The procedures of Example 18 were repeated except that the starting expanded material made according to Example 9 was made from a functional resin containing 1.4 mol % (6.1 wt %) PSVE made according to Example 5. This membrane had a mass per area of 1.6 g/m$^2$. The initial coating draw down gap was 6 mil (150 microns) and the second draw down gap was 3 mil (75 microns). The final measured thickness of this imbibed composite membrane was 12±2 microns. The imbibed composite material produced in this example also successfully performed as a solid polymer electrolyte as indicated by the polarization curve obtained from the MEA prepared from the material.

EXAMPLE 21

The procedures of Example 18 were repeated except that the —SOOF pendant groups in the starting expanded material containing 1.7 mol % (7.7 wt %) PSVE were converted to the acid form, —SO$_3$H. The starting membrane was first wetted with IPA and then immersed in a 20 wt % KOH solution (Aldrich) at 100° C. for 72 hours. It was then rinsed with DI water and was immersed in 15 wt % nitric acid (Aldrich) at 80° C. for 24 hours. The converted membrane was further boiled in DI water at 15 psig for 60 hours and then air dried at room temperature. The starting membrane had a mass per area of 5.2 g/m$^2$. The imbibed composite membrane had a thickness of 12±2 microns. The imbibed composite material produced in this example also successfully performed as a solid polymer electrolyte as indicated by the polarization curve obtained from the MEA prepared from the material.

EXAMPLE 22

The procedures of Example 21 were repeated except that the starting expanded material containing 1.4 mo % (6.1 wt %) PSVE had a mass per area of 1.6 g/m$^2$. The —SOOF pendent groups in the membrane were converted to the acid form, —SO$_3$H. The membrane was converted and then boiled in DI water according to Example 21. The final measured thickness of this imbibed composite membrane was 12±2 microns. The imbibed composite material produced in this example also successfully acted as a solid polymer electrolyte as indicated by the polarization curve obtained from the MEA prepared from the material.

EXAMPLE 23

Three beads were prepared by paste extrusion of three different polymers as described below:

Polymer A)

A fine powder resin comprising the copolymer of TFE and PSVE having 1.1 mol % PSVE. The break strength of the beading was 28.5 N.

Polymer B)

A fine powder resin comprising a copolymer of TFE and PSVE having 1.0 mol % PSVE was comprised of a blend of 30% by weight copolymer of TFE and PSVE having a 3.6 mol % of PSVE, and 70% by weight modified TFE made in accordance with the teachings of U.S. Pat. No. 6,541,589.

Polymer C)

A fine powder resin comprising a copolymer of TFE and PSVE having 1.1 mol % PSVE was comprised of a blend of 80% by weight copolymer of TFE and PSVE having a 0.7 mol % of PSVE, and 20% by weight copolymer of TFE and PSVE having a 2.7 mol % of PSVE.

A 113.4 g sample of each polymer resin was blended together with Isopar® K at a ratio of approximately 0.250 g/g of resin. The blend was conditioned at 49° C. for 10-12 hours. A 2.54 cm diameter cylindrical preform was made by applying about 1,860 kPa of preforming pressure for about 20 seconds. The extruder barrel was 2.54 cm in diameter and the ram rate of movement was approximately 1.5 cm/min. The Isopar® K was removed from the beading by drying the beading in a restrained manner at 49° C. for about 24 hours.

The break Strength of the beading was measured using an Instron® tensile tester using an initial sample length of 2.54 cm and a crosshead speed of 2.54 cm/min. Results for matrix tensile strength reported in Table 8 are the average of 3 or more tests.

TABLE 8

Beading Matrix Tensile Strength

| | Matrix Tensile Strength (kPa) |
|---|---|
| Polymer A | 7,612 |
| Polymer B | 7,302 |
| Polymer C | 6,343 |

Approximately the first and last 2.5 m of the extruded beading were discarded to eliminate end effects. A 1.9 cm section of the extruded beading was expanded at a ration of approximately 35:1, by stretching at 250° C. to at a constant true strain rate of 1 s$^{-1}$ (the engineering rate at the start of expansion is 100%/s). Approximately a 30 cm length from near the center of the expanded beading was removed, and the maximum break load of the removed sample held at room temperature (23° C. plus or minus 1.5° C.) is measured using an Instron® tensile tester using an initial sample length of 2.54 cm and a crosshead speed of 2.54 cm/min. The matrix tensile strength was calculated from the maximum break load and the mass of the sample tested.

TABLE 9

Expanded Beading Matrix Tensile Strength

| | Matrix Tensile Strength (kPa) |
|---|---|
| Polymer A | 171,096 |
| Polymer B | 194,156 |
| Polymer C | 126,607 |

The expanded beading was then wet with IPA and submersed in 20% by weight % KOH in water at 175° C. for 4 hours. The expanded beading was then removed, rinsed with de-ionized water and submersed in 15% by weight nitric acid in water at a temperature of 175° C. for 4 hours. The expanded beading was then removed, rinsed and air dried.

The samples were then submersed in water and only the expanded beading made with the blend of two functional TFE copolymers, Polymer C, was hydrophilic as it became translucent.

We claim:

1. An expanded copolymeric material comprising;
   (a) a functional tetrafluoroethylene (TFE) copolymer material comprising:
      a first portion comprising a polymer chain of TFE and at least two comonomers, each said comonomer having a functional group pendant to the polymer chain; and
      a second, shell portion comprising a functional TFE copolymer having high crystallinity; and
   (b) at least one additional fluoropolymer,
   wherein said at least two comonomers provide different functional groups.

2. The expanded copolymeric material of claim 1, wherein the at least one additional fluoropolymer is a second functional TFE copolymer.

3. The expanded copolymeric, material of claim 1, wherein the at least one additional fluoropolymer is a PTFE polymer.

4. The expanded copolymeric material of claim 1, wherein the at least one additional fluoropolymer is a modified PTFE polymer.

5. The expanded copolymeric material of claim 1, wherein the at least one comonomer is a fluorovinyl ether comonomer of the general formula $CF_2=CF-OR_fZ$, where $R_f$ represents a fluoro alkyl group optionally interrupted by one or more oxygen(s) and Z represents a functional group.

6. The expanded copolymeric material of claim 5. wherein Z is selected from the group consisting of carboxylic acid or salts thereof, sulfonyl halide, sulfonic acid or salts thereof, sulfonamide, sulfonimide, phosphonic acid or salts thereof, cyano, isocyanate and combinations thereof.

7. The expanded copolymeric material of claim 1, wherein the at least one functional group is selected from the group consisting of carboxylic acid or salts thereof, sulfonyl halide, sulfonic acid or salts thereof, sulfonamide, sulfonimide,-phosphonic acid or salts thereof, cyano, isocyanate and combinations thereof.

8. The expanded copolymeric material of claim 1, wherein said first portion further comprises at least one comonomer that does not contain a pendant functional group.

9. The expanded copolymeric material of claim 1, wherein the expanded copolymeric material is microporous.

10. The expanded copolymeric material of claim 1, wherein the at least two comonomers are present in the copolymer in an amount between 0.01 mol% and 5 mol% of the copolymer.

11. An expanded copolymeric material comprising:
(a) a functional TFE copolymer material comprising:
  a first portion comprising a polymer chain of TFE and at least one comonomer having a functional group that is pendant to the polymer chain: and
  a second, shell portion having high crystallinity comprising polymerized TFE monomers; and
(b) at least one additional fluoropolymer,
wherein said first portion further comprises at least one comonomer that does not contain a pendant functional group.

12. The expanded copolymeric material of claim 11, wherein the first portion comprises at least two comonomers.

13. The expanded copolymeric material of claim 11, wherein the first portion comprises at least two comonomers, each said comonomer having a different functional group.

14. The expanded copolymeric material of claim 11, wherein the at least one additional fluoropolymer is a second functional TFE copolymer.

15. The expanded copolymeric material of claim 11, wherein the at least one additional fluoropolymer is a PTFE polymer.

16. The expanded copolymeric material of claim 11, wherein the at least one additional fluoropolymer is a modified PTFE polymer.

17. The expanded copolymeric material of claim 11, wherein the at least one comonomer is a fluorovinyl ether comonomer of the general formula $CF_2=CF-OR_fZ$, where $R_f$ represents a fluoro alkyl group optionally interrupted by one or more oxygen(s) and Z represents a functional group.

18. The expanded copolymeric material of claim 17, wherein Z is selected from the group consisting of carboxylic acid or salts thereof. sulfonyl halide, sulfonic acid or salts thereof, sulfonamide, sulfonimide, phosphonic acid or salts thereof, cyano, isocyanate and combinations thereof.

19. The expanded copolymeric material of claim 11, wherein the at least one functional group is selected from the group consisting of carboxylic acid or salts thereof, sulfonyl halide, sulfonic acid or salts thereof, sulfonamide, sulfonimide,-phosphonic acid or salts thereof, cyano, isocyanate and combinations thereof.

20. The expanded copolymeric material of claim 12, wherein said at least two comonomers provide different functional groups.

21. The expanded copolymeric material of claim 12, wherein said at least two comonomers provide the same functional groups.

22. The expanded copolymeric material of claim 11, wherein the expanded copolymeric material is microporous.

23. The expanded copolymeric material of claim 11, wherein the at least one comonomer is present in the copolymer in an amount between 0.01 mol% and 5 mol% of the copolymer.

* * * * *

UNITED STATES PATENT AND TRADEMARK OFFICE
CERTIFICATE OF CORRECTION

PATENT NO.         : 8,809,407 B2
APPLICATION NO.    : 13/684955
DATED              : August 19, 2014
INVENTOR(S)        : Xu et al.

It is certified that error appears in the above-identified patent and that said Letters Patent is hereby corrected as shown below:

In the Specification

At column 1, line 28: change "use high" to --use: high--

At column 2, line 61: change "$CF_{2=CF-OR_f}COOCH_3$" to --$CF_2=CF-OR_fCOOCH_3$--

At column 10, line 26: change "know" to --known--

At column 11, line 2: change "nitrite" to --nitrile--

At column 11, line 9: change "nitrite" to --nitrile--

At column 11, line 23: change "nitrite" to --nitrile--

At column 11, line 40: change "know" to --known--

At column 15, line 17: change "homopolyfuntional" to --homopolyfunctional--

At column 15, line 18: change "heteropolyfuntional" to --heteropolyfunctional--

At column 26, lines 16-17: change "Wu et. al. (2008/007036)" to --Berta et al. (2007/0072036)--

At column 28, line 18: change "ration" to --ratio--

Signed and Sealed this
Eighteenth Day of November, 2014

Michelle K. Lee
*Deputy Director of the United States Patent and Trademark Office*